US012661065B2

(12) United States Patent
Takahashi et al.

(10) Patent No.: US 12,661,065 B2
(45) Date of Patent: Jun. 23, 2026

(54) SHEET-TYPE INCLUDING FIRST AND SECOND SENSORS TO ACQUIRE INFORMATION OF A USER DEVICE AND SYSTEM

(71) Applicant: PARAMOUNT BED CO., LTD., Tokyo (JP)

(72) Inventors: Nozomu Takahashi, Tokyo (JP); Mao Yoshida, Tokyo (JP); Takumi Taketomi, Tokyo (JP); Junko Nishimura, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 305 days.

(21) Appl. No.: 18/384,461

(22) Filed: Oct. 27, 2023

(65) Prior Publication Data

US 2024/0335167 A1 Oct. 10, 2024

(30) Foreign Application Priority Data

Apr. 7, 2023 (JP) ................................. 2023-062728

(51) Int. Cl.
*A61B 5/00* (2006.01)
*G01G 19/44* (2006.01)

(52) U.S. Cl.
CPC .......... *A61B 5/6804* (2013.01); *A61B 5/4561* (2013.01); *A61B 5/746* (2013.01); *G01G 19/445* (2013.01); *A61B 2562/0247* (2013.01); *A61B 2562/04* (2013.01)

(58) Field of Classification Search
CPC ... G01G 19/445; A61B 5/1115; A61B 5/1116; A61B 5/6892; A61B 2562/0247; A61B 2562/04
See application file for complete search history.

(56) References Cited

U.S. PATENT DOCUMENTS

| | | | |
|---|---|---|---|
| 2004/0010202 A1* | 1/2004 | Nakatani ................ | A61B 5/113 600/529 |
| 2005/0113711 A1* | 5/2005 | Nakatani .............. | A61B 5/1126 600/595 |
| 2005/0124864 A1* | 6/2005 | Mack ................... | A61B 5/6892 600/587 |
| 2008/0169931 A1* | 7/2008 | Gentry ................. | A61B 5/1117 600/300 |

(Continued)

FOREIGN PATENT DOCUMENTS

| | | | |
|---|---|---|---|
| CN | 209764314 U | * | 12/2019 |
| JP | 2015-8920 | | 1/2015 |
| JP | 2021-194530 | | 12/2021 |

OTHER PUBLICATIONS

Machine translation of CN-209764314 (Year: 2019).*

*Primary Examiner* — Natalie Huls
(74) *Attorney, Agent, or Firm* — Wenderoth, Lind & Ponack, L.L.P.

(57) ABSTRACT

A sheet-type device that can be arranged under a user, the sheet-type device including: a plurality of first sensors configured to acquire a weight of the user, a second sensor configured to acquire biological information of the user, and a controller configured to acquire values acquired from the first sensors and to determine a state of the user, wherein the first sensors and the second sensor are arranged in one line along a right-left direction of the user, and the second sensor is arranged between the first sensors.

16 Claims, 23 Drawing Sheets

(56)          References Cited

U.S. PATENT DOCUMENTS

| | | | |
|---|---|---|---|
| 2015/0119656 A1* | 4/2015 | Foster .................... | A61B 5/746 |
| | | | 600/301 |
| 2016/0007887 A1* | 1/2016 | Shimizu .............. | G08B 29/185 |
| | | | 340/573.4 |
| 2017/0156638 A1* | 6/2017 | Ribble ................... | A61G 7/018 |
| 2018/0146917 A1* | 5/2018 | Iida ....................... | A61B 5/1116 |
| 2020/0178887 A1* | 6/2020 | Correa Ramírez .. | A61B 5/4809 |
| 2021/0106256 A1* | 4/2021 | Kogure ................... | A61G 7/05 |
| 2021/0295661 A1* | 9/2021 | Tadele ................ | A61B 5/6892 |
| 2023/0061572 A1* | 3/2023 | Faizan .................. | A61B 5/746 |

* cited by examiner

MAIN SENSOR DEVICE

OPTIONAL SENSOR DEVICE

102

102

104

102

106

120

120

| DATE/TIME | 40A | 40B | 40C | 40D |
|---|---|---|---|---|
| ⋮ | ⋮ | ⋮ | ⋮ | ⋮ |
| 2023/03/10 23:10:00 | 50 | 100 | 120 | 70 |
| 2023/03/10 23:10:30 | 30 | 70 | 100 | 100 |
| ⋮ | ⋮ | ⋮ | ⋮ | ⋮ |

| DATE/TIME | 40A | 40B | 40C | 40D |
|---|---|---|---|---|
| AREA R10 | 80 | 80 | – | – |
| AREA R12 | – | 80 | 80 | – |
| AREA R14 | – | – | 80 | 80 |

| DATE/TIME | 40A | 40B | 40C | 40D | 45A | 45B | 45C | 45D |
|---|---|---|---|---|---|---|---|---|
| ⋮ | ⋮ | ⋮ | ⋮ | ⋮ | ⋮ | ⋮ | ⋮ | ⋮ |
| 2023/03/10 23:10:00 | 50 | 100 | 120 | 70 | 30 | 80 | 100 | 50 |
| 2023/03/10 23:10:30 | 30 | 70 | 100 | 100 | 10 | 50 | 80 | 80 |
| ⋮ | ⋮ | ⋮ | ⋮ | ⋮ | ⋮ | ⋮ | ⋮ | ⋮ |

NOTIFICATION AREA SETTING PROCESSING

W100

SELECT AREA TO NOTIFY
WHEN USER IS PRESENT.

⬜ NOTIFY　　⬜ NOT NOTIFY

RETURN　　SET

| FIRST AREA | SECOND AREA | THIRD AREA |
|---|---|---|
| NOTIFY | NOT NOTIFY | NOTIFY |

| FIRST AREA | SECOND AREA | THIRD AREA |
|---|---|---|
| NOTIFY (LOW) | NOT NOTIFY | NOTIFY (HIGH) |

| | 40A | 40B | 40C | 40D |
|---|---|---|---|---|
| NOTIFY | 100 OR LARGER | 30 OR SMALLER | 30 OR SMALLER | 30 OR SMALLER |

FIG. 18A
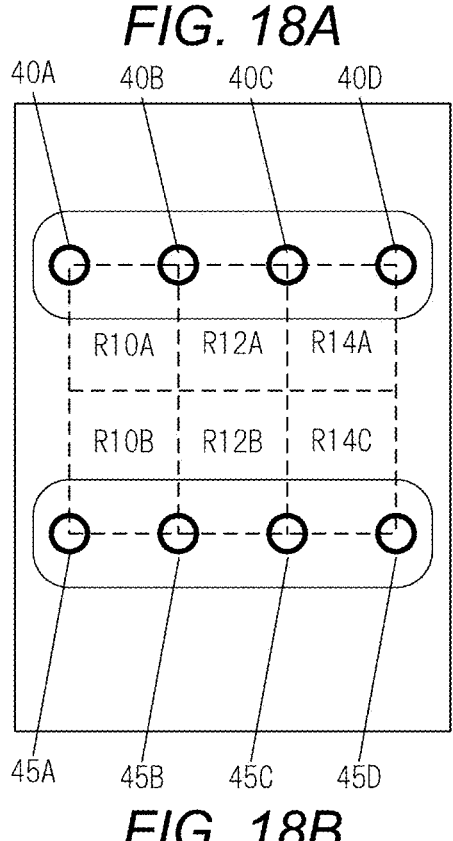
FIG. 18B
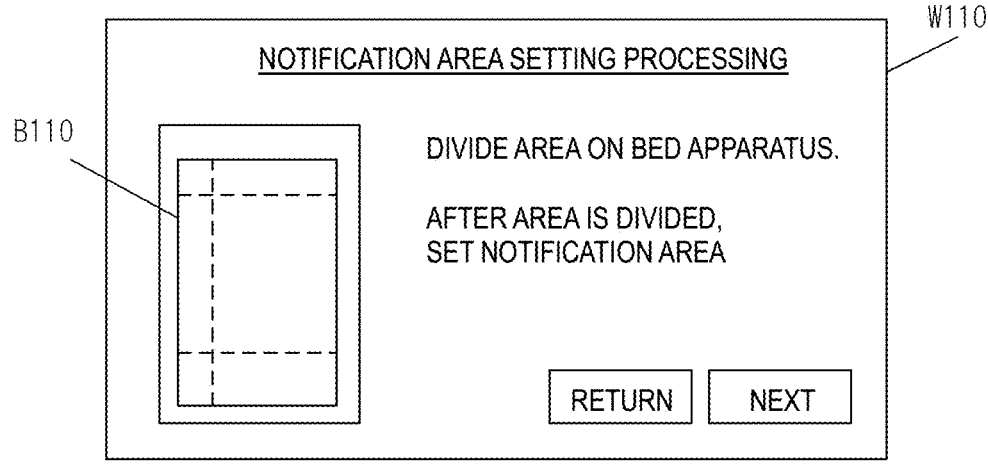
FIG. 18C
| DATE/TIME | 40A | 40B | 40C | 40D | 45A | 45B | 45C | 45D |
|-----------|-----|-----|-----|-----|-----|-----|-----|-----|
| AREA 10A | 80 | 80 | — | — | 50 | 50 | — | — |
| AREA 10B | 50 | 50 | — | — | 80 | 80 | — | — |
| ⋮ | ⋮ | ⋮ | ⋮ | ⋮ | ⋮ | ⋮ | ⋮ | ⋮ |

FIG. 19

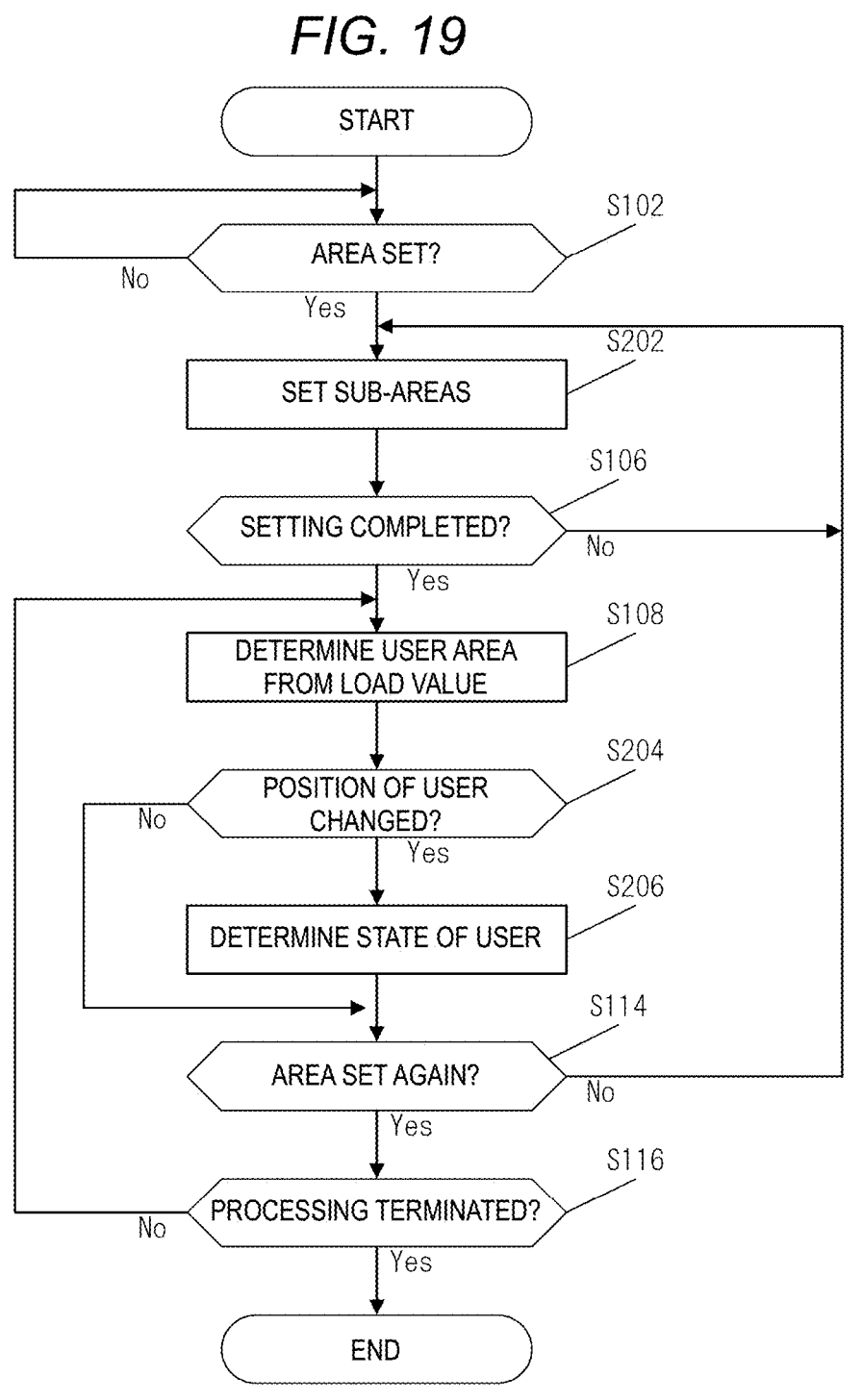

START

↓

S102 — AREA SET? — No (loops back)

Yes ↓

S202 — SET SUB-AREAS

↓

S106 — SETTING COMPLETED? — No →

Yes ↓

S108 — DETERMINE USER AREA FROM LOAD VALUE

↓

S204 — POSITION OF USER CHANGED? — No

Yes ↓

S206 — DETERMINE STATE OF USER

↓

S114 — AREA SET AGAIN? — No

Yes ↓

S116 — PROCESSING TERMINATED? — No

Yes ↓

END

FIG. 20A
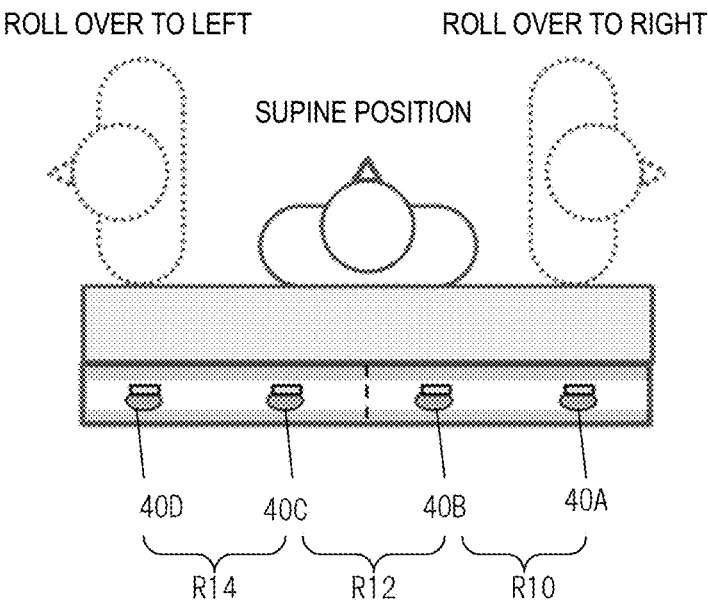
ROLL OVER TO LEFT    ROLL OVER TO RIGHT
SUPINE POSITION
40D    40C    40B    40A
R14    R12    R10
FIG. 20B
| DATE/TIME | 40A | 40B | 40C | 40D |
|---|---|---|---|---|
| NOT DETERMINE | 80 | 80 | – | 80 |
FIG. 20C
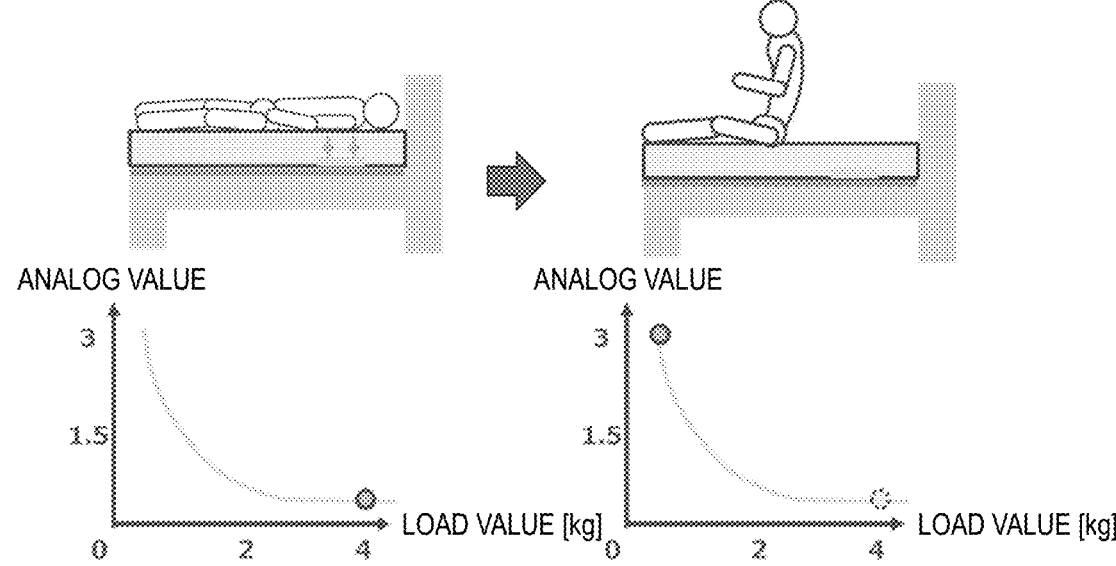
ANALOG VALUE    ANALOG VALUE
LOAD VALUE [kg]    LOAD VALUE [kg]

FIG. 21

| SENSOR DEVICE 10 | SENSOR DEVICE 15 | STATE OF USER |
|---|---|---|
| SLEEPING | - (NOT CONNECTED) | SLEEPING |
| WAKING-UP | - (NOT CONNECTED) | WAKING-UP |
| SITTING-UP | - (NOT CONNECTED) | SITTING-UP |
| UNDETECTED | - (NOT CONNECTED) | UNDETECTED |
| SLEEPING | BED PRESENCE | SLEEPING |
| SLEEPING | UNDETECTED | SLEEPING |
| WAKING-UP | BED PRESENCE | WAKING-UP |
| WAKING-UP | UNDETECTED | WAKING-UP |
| WAKING-UP | EDGE SITTING POSITION | EDGE SITTING POSITION |
| WAKING-UP | BED DEPARTURE | BED DEPARTURE |
| SITTING-UP | BED PRESENCE | SITTING-UP |
| SITTING-UP | UNDETECTED | SITTING-UP |
| SITTING-UP | EDGE SITTING POSITION | EDGE SITTING POSITION |
| SITTING-UP | BED DEPARTURE | BED DEPARTURE |
| UNDETECTED | BED PRESENCE | WAKING-UP |
| UNDETECTED | UNDETECTED | BED DEPARTURE |
| UNDETECTED | EDGE SITTING POSITION | EDGE SITTING POSITION |
| UNDETECTED | BED DEPARTURE | BED DEPARTURE |

SHEET-TYPE INCLUDING FIRST AND SECOND SENSORS TO ACQUIRE INFORMATION OF A USER DEVICE AND SYSTEM

BACKGROUND OF THE INVENTION

Field

The present disclosure relates to a state acquisition device and the like.

Background

For example, as disclosed in JP2015-008920A and JP2021-194530A, the inventions of acquiring a state of a user on a bed apparatus have been available.

BRIEF DESCRIPTION OF THE DRAWINGS

FIG. 18A is a view illustrating a modified example of the areas in the embodiment, FIG. 18B is a view illustrating another example of the setting of the areas in the embodiment, and FIG. 18C is a table illustrating another example of the set areas in the embodiment.

FIG. 19 is a flowchart illustrating processing in the embodiment.

FIGS. 20A to 20C illustrate the motion in the embodiment.

FIG. 21 is a table illustrating the motion in the embodiment.

DETAILED DESCRIPTION

Figure 1:
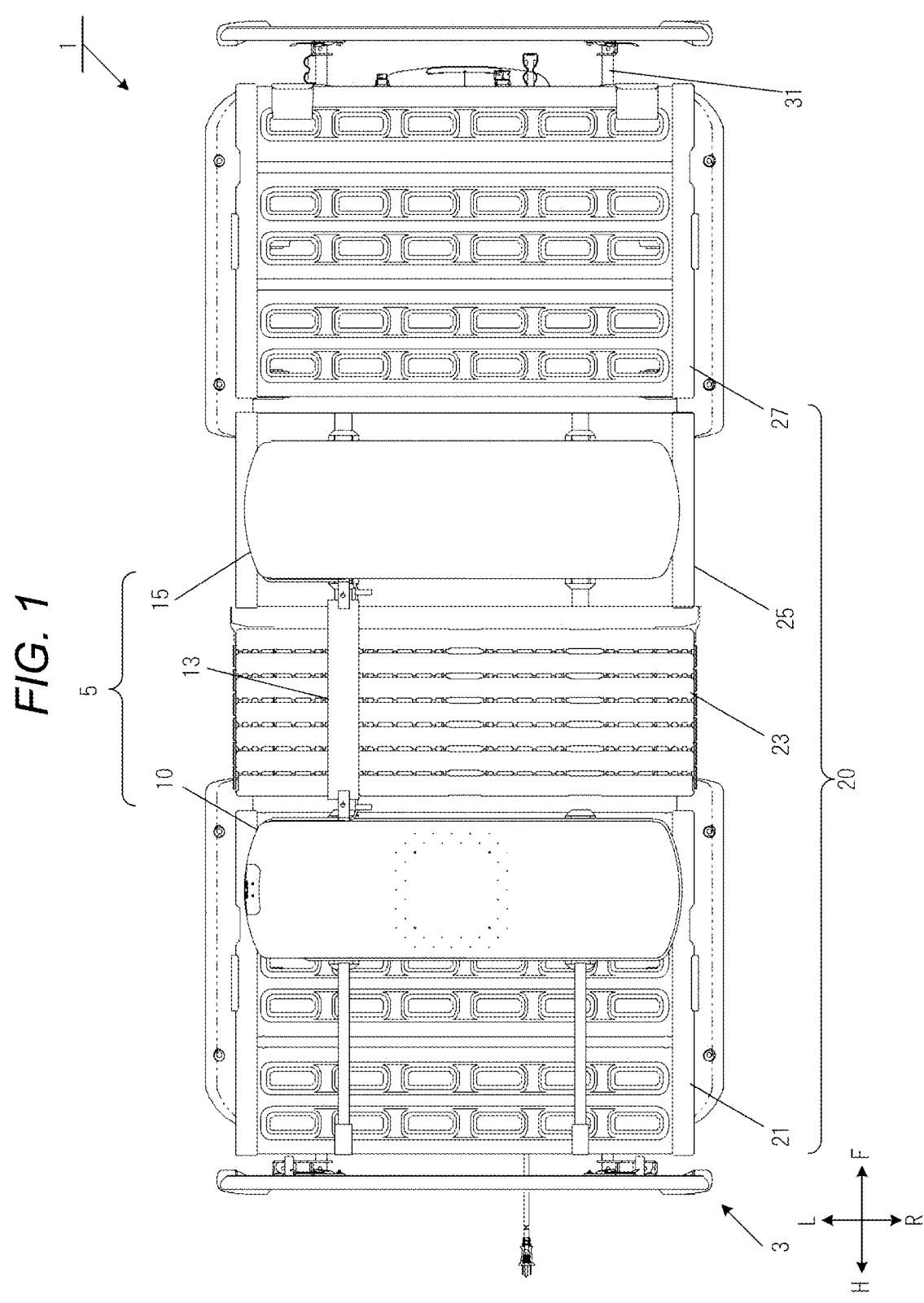
FIG. 1 is a view illustrating an entire bed apparatus and an entire acquisition apparatus in an embodiment.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component", "system" and the like are intended to refer to, or comprise, a computer-related entity or an entity related to an operational apparatus with one or more specific functionalities, wherein the entity can be either hardware, or a combination of hardware and software in execution.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software stored on a non-transitory electronic memory or firmware that confers at least in part the functionality of the electronic components. While various components have been illustrated as separate components, it will be appreciated that multiple components can be implemented as a single component, or a single component can be implemented as multiple components, without departing from example embodiments. Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer-readable (or machine-readable) device or computer-readable (or machine-readable) storage/communications media having a computer program stored thereon. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

In general, one aspect of the present application is a sheet-type device that can be arranged under a user, the sheet-type device including: a plurality of first sensors configured to acquire a weight of the user, a second sensor configured to acquire biological information of the user, and a controller configured to acquire values acquired from the first sensors and to determine a state of the user, wherein the first sensors and the second sensor are arranged in one line along a right-left direction of the user, and the second sensor is arranged between the first sensors.

Another aspect of the present application is a system including: a first sheet-type device that can be arranged on a bed apparatus and in which a plurality of first pressure-sensitive sensors are arranged in a longitudinal direction, and a second sheet-type device that can be arranged on the bed apparatus and in which a plurality of second pressure-sensitive sensors are arranged in a longitudinal direction, wherein the first sheet-type device is arranged at a first position of the bed apparatus such that the first pressure-sensitive sensors are arranged at equally-spaced intervals along a width direction of the bed apparatus, the second sheet-type device is arranged at a second position of the bed apparatus such that the second pressure-sensitive sensors are arranged at equally-spaced intervals along the width direction of the bed apparatus, the second position being different from the first position and the first sheet-type device is configured: to acquire, from the second sheet-type device, values acquired by the second pressure-sensitive sensors, and to acquire a state of the user on the bed apparatus based on the values acquired from the first pressure-sensitive sensors and values acquired from the second acquisition device.

A description will hereinafter be made on an embodiment for implementing the present disclosure with reference to the drawings. The embodiment, which will be described below, is an embodiment for providing the present disclosure and should not be construed as limiting contents of the present disclosure based on the following description.

In general, a sheet-type apparatus that is spread out under a user to acquire the user's state has been known. For example, a sheet-type sensor that is usable on a bed apparatus can detect sitting up of the user and can detect bed departure or bed presence of the user. The sensor makes these types of detection only based on an internal pressure change in a pneumatic sensor tube (for example, it is determined that the user has sat up when the pressure becomes a predetermined pressure or lower), for example.

However, the sheet-type sensor that has been used so far only uses a single detection parameter, and the detection parameter is the pressure change that is based on the sensor output. Accordingly, it is only possible to detect whether the user is lying on the bed apparatus.

In addition, the above sensor makes the detection based on a change amount in the internal pressure per unit time. Accordingly, in the case where the user slowly moves on a mattress that is placed on the sheet-type sensor, a detection condition is no longer satisfied, and rising of the user cannot be detected. Furthermore, in the case where the user is lying on a lower-half side of the mattress or the user is a lightweight, the internal pressure in the pneumatic tube does not change, which interferes with the detection of sitting up of the user, and the like.

A system alarming that the user possibly falls according to a position of the user on the mattress has been available. In such a system, a device that detects falling has to be provided outside the bed apparatus and thus occupies too much space. A system that images the user on the mattress with a camera to alarm possible falling of the user has also been available. However, since the user is imaged with the camera all the time, such a system has a privacy issue.

Furthermore, a system that determines the position of the user on the bed apparatus based on a load change has been known. For example, a load sensor is provided to a leg unit or under the leg unit of the bed apparatus, and a space on the bed apparatus is set as a virtual area to acknowledge the position of the user.

However, in the case where the load sensor for the virtual space where the position of the user is detected is incorporated in the bed apparatus, the bed, in which the load sensor is incorporated, has to be prepared for each user.

A technique disclosed in the present disclosure is proposed to solve one or more of such problems. A description will hereinafter be made on an embodiment related to a system that includes an acquisition device according to the present disclosure.

The user means a person who lies on the bed apparatus including a sensor device or a person who uses the bed apparatus. The users are not limited to a sick person and a person who needs nursing care but also are a healthy person. In addition, the user includes not only an adult and an elderly adult but also a child and the like.

Staff members include a healthcare professional at a hospital where the user stays, a worker at a facility where the user stays, and the like. In the case of the user's house, the staff members also include a family member who nurses or cares for the user.

1. Overall Configuration

FIG. 1 is a view illustrating an entire bed system 1. An acquisition apparatus 5 is provided on a bed apparatus 3.

In the bed apparatus 3, sections 20 are provided on a frame 31. When seen from the user who lies supine on the bed apparatus 3 in FIG. 1, for example, the sections 20 have, from a head side (H side) toward a foot side (F side), a back section 21, a seat section (Kyma line section) 23, an upper leg section 25, and a lower leg section 27. A right side of the user (at a supine position) on the bed apparatus is set as an R side while a left side thereof is set as an L side.

The bed apparatus 3 can perform a back raise movement (back lower movement) and a knee raise movement (knee lower movement), for example, by moving the back section 21, the seat section 23, and the like. The bed apparatus 3 has a general configuration. For example, as illustrated in FIG. 1, the bed apparatus 3 may be provided with a head board and a foot board, and may be provided with holes for providing a side rail. The bed apparatus 3 may also has a drive unit (actuator) to change a shape of the bed apparatus 3 by moving each of the sections as described above and to change a height of the bed apparatus 3 by raising or lowering the frame 31.

The acquisition apparatus 5 is a sheet-shaped sensor capable of acquiring a state, a movement, and the like of the user, and is located under the user. For example, the acquisition apparatus 5 can be arranged on the bed apparatus 3. The phrase "arrange (or place) the acquisition apparatus 5 on the bed apparatus 3" means arranging the acquisition apparatus 5 such that the acquisition apparatus 5 is closer to the user than the sections 20 of the bed apparatus 3 is. For example, as a specific arrangement method of the acquisition apparatus 5, the acquisition apparatus 5 is arranged to be sandwiched between the sections 20 of the bed apparatus 3 and the mattress or a futon (hereinafter, the mattress or the like). The acquisition apparatus 5 may be arranged on the mattress or the like, for example. That is, the acquisition apparatus 5 is arranged to be located under the user. Accordingly, when the user lies on the futon that is spread on tatamis or a floor, the acquisition apparatus 5 only needs to be located under the user. In this case, the acquisition apparatus 5 only needs to be arranged on the futon or under the futon (on the tatamis or the floor).

In addition, for example, a state acquisition device 10 and an optional movement acquisition device 15 connectable to the state acquisition device 10 can be connected to the acquisition apparatus 5. Here, the state acquisition device 10 is an example of the state acquisition device capable of acquiring a state of the user, for example, based on a load value and vibration acquired from plural types of sensors, and is a main sensor device. For example, the movement acquisition device 15 is a sensor device that acquires the load value from a pressure-sensitive sensor, and is an optional sensor device. The movement acquisition device 15 is preferably provided when necessary. That is, the state acquisition device 10 may be a sensor device that acquires the state of the user, and the movement acquisition device 15 may be a simple sensor device that acquires a load. The movement acquisition device 15 is a device capable of detecting a movement of the user, and may be referred to as a movement detector or simply as a detector.

Here, the state of the user in this embodiment indicates a state related to the user and includes states as described below.

A state of bed presence or bed departure of the user

A sleep state of the user (for example, sleep, an awake state, depth of sleep (REM sleep, non-REM sleep, or the like), or the like)

A posture state of the user (for example, a standing position, an edge sitting position, a lying position, or the like)

A state of a sleeping posture (the supine position, a lateral position, a prone position, or the like) and a sleeping position of the user.

A state based on the biological information of the user (the heartbeat, the respiration, SpO2, a blood pressure, a body temperature, and the like)

Here, states other than the state based on the biological information of the user may be divided as a first state from the state based on the biological information as a second state. The state acquisition device 10 can acquire the first state of the user and the second state of the user with different types of sensors.

In FIG. 1, the state acquisition device 10 is provided on the back section 21 as a first position. The state acquisition device 10 can detect the movement of the user (for example, motion based on the movement of the user, minute motion such as the heartbeat or the respiration of the user, body movement, or the like) on the state acquisition device 10. The state acquisition device 10 can acquire, for example, the state such as the bed presence/bed departure of the user, the posture of the user, the state such as the sleeping posture, or the biological information such as a heartbeat rate or a respiratory rate of the user based on the detected movement of the user. Here, the first position is preferably near the head side of the bed apparatus 3, and is more preferably a position near the user's back when the user is at the supine position.

The state acquisition device 10 can be connected to the optional movement acquisition device 15 via a cable 13. Basically, a configuration of the movement acquisition device 15 to acquire (detect) the movement (motion) of the user is based on the state acquisition device 10, and a part of the configuration thereof may not be provided. For example, some of the functions (such as a sensor capable of acquiring the biological information including the heartbeat, the respiration, and the like of the user, a wireless communication function, and the like) provided by the state acquisition device 10 may not be provided. In addition, in the case where the same device as the state acquisition device 10 is used, such a device may substitute the movement acquisition device 15 by switching master/slave by setting, for example.

As a second position, the movement acquisition device 15 is provided on the upper leg section 25, for example. Compared to the first position, the second position is preferably located near the foot side of the bed apparatus 3. In this embodiment, the second position is located on the upper leg section 25 so as to be able to easily fix a position of the movement acquisition device 15.

Here, preferably, there is a play when the state acquisition device 10, which is provided on the back section 21, is installed. Due to presence of a play at the installed position of the state acquisition device 10, even when the back section 21 is raised or lowered, for example, the state acquisition device 10 is installed at an appropriate position regardless of displacement of the mattress, which is placed on the back section 21, or the like.

The movement acquisition device 15 is preferably fixed at a position on the upper leg section 25. Preferably, the movement acquisition device 15 is not displaced from the originally installed position, for example, even when the upper leg section 25 is raised or lowered.

As described above, the state acquisition device 10 is installed at the position corresponding to the back of the user at the supine position on the bed apparatus 3 (the mattress or the like). Meanwhile, the movement acquisition device 15 is installed in an area from a position near a lower back part to a position near a thigh part of the user at the supine position on the bed apparatus 3 (the mattress or the like).

2. Configuration of Acquisition Apparatus

Figures 2A, 2B:
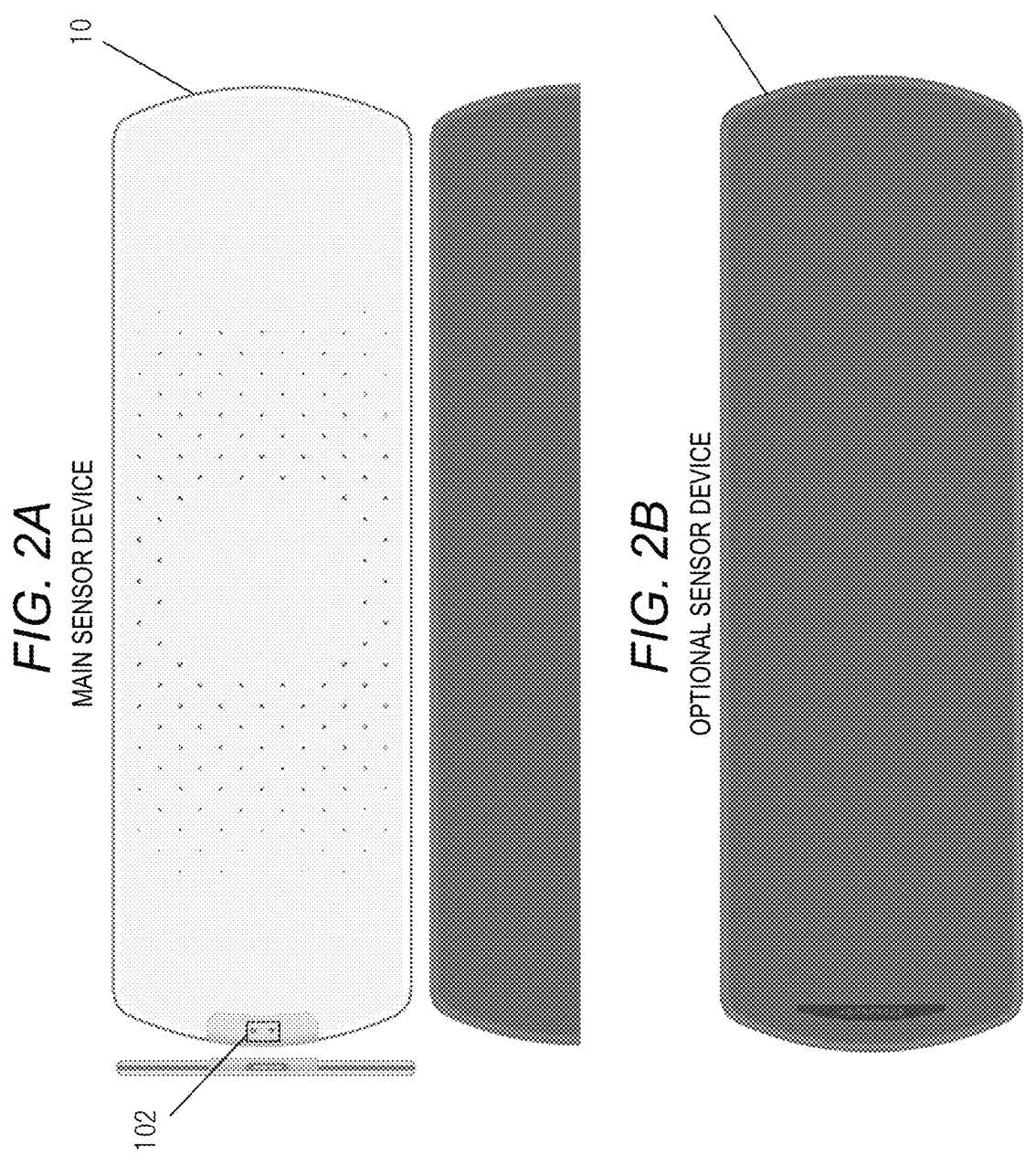
FIG. 2A is a view illustrating external appearance of a state acquisition device in the embodiment.
FIG. 2B is a view illustrating external appearance of a movement acquisition device in the embodiment.

A description will hereinafter be made on configurations of the state acquisition device 10 and the movement acquisition device 15. For example, a description will be made on the configurations thereof in the case where the state acquisition device 10 functions as a main sensor and the movement acquisition device 15 functions as an optional sensor.
Entire Acquisition Apparatus FIGS. 2A and 2B illustrate external appearance of the acquisition apparatus 5. FIG. 2A illustrates external appearance of the state acquisition device 10, and FIG. 2B illustrates external appearance of the movement acquisition device 15. In this case, the state acquisition device 10 in FIG. 2A functions as the main sensor device, and the movement acquisition device 15 in FIG. 2B functions as an optional sensor device.

The state acquisition device 10 has a thin, simple structure. The state acquisition device 10 has a controller on one end side, and may also have a notification section notifying a state of the state acquisition device 10. For example, in FIG. 2A, the state acquisition device 10 may have an indicator that indicates a state of a power supply and an indicator that indicates a communication state of the state acquisition device 10.

The state acquisition device 10 may show necessary information on a lateral surface. For example, FIG. 2A includes a side view, and a serial number may be illustrated in the side view. In addition, the state acquisition device 10 may be provided with an LED on the lateral side and thereby show the necessary information by a lit state of the LED. For example, the state acquisition device 10 may show the communication state with another device by the LED. The state acquisition device 10 may blink the LED in an interlocking manner with the biological information (for example, the respiration or the heartbeat) of the user. Furthermore, the state acquisition device 10 may be provided with a liquid crystal display or a display including an organic EL display on the lateral surface. The state acquisition device 10 may show, on the display, information that is based on the biological information of the user.

The state acquisition device 10 is used for each of the plural bed apparatuses 3 at a hospital or a facility, for example. At this time, in the case where various types of the information are displayed on the lateral surface of the state acquisition device 10 as described above, a staff member or the like can identify the state acquisition device 10 simply by seeing the lateral surface of the state acquisition device 10 when checking a correspondence between the bed apparatus 3 (that is, the user who uses the bed apparatus 3) and the state acquisition device 10.

As illustrated in FIG. 2B, design of the movement acquisition device 15 may differ from that of the state acquisition device 10. For example, the state acquisition device 10 has a white upper surface and a dark gray back surface. The movement acquisition device 15 may be colored dark gray for all surfaces, so as to be differentiated from the state acquisition device 10.

In addition, unlike the state acquisition device 10, the movement acquisition device 15 has simple design without a pattern and an edge tape. Thus, even when the state acquisition device 10 is replaced with a new device, the movement acquisition device 15 may be used as is. At this time, due to the simple design, the movement acquisition device 15 can be used without giving a sense of discomfort.

Figure 3:
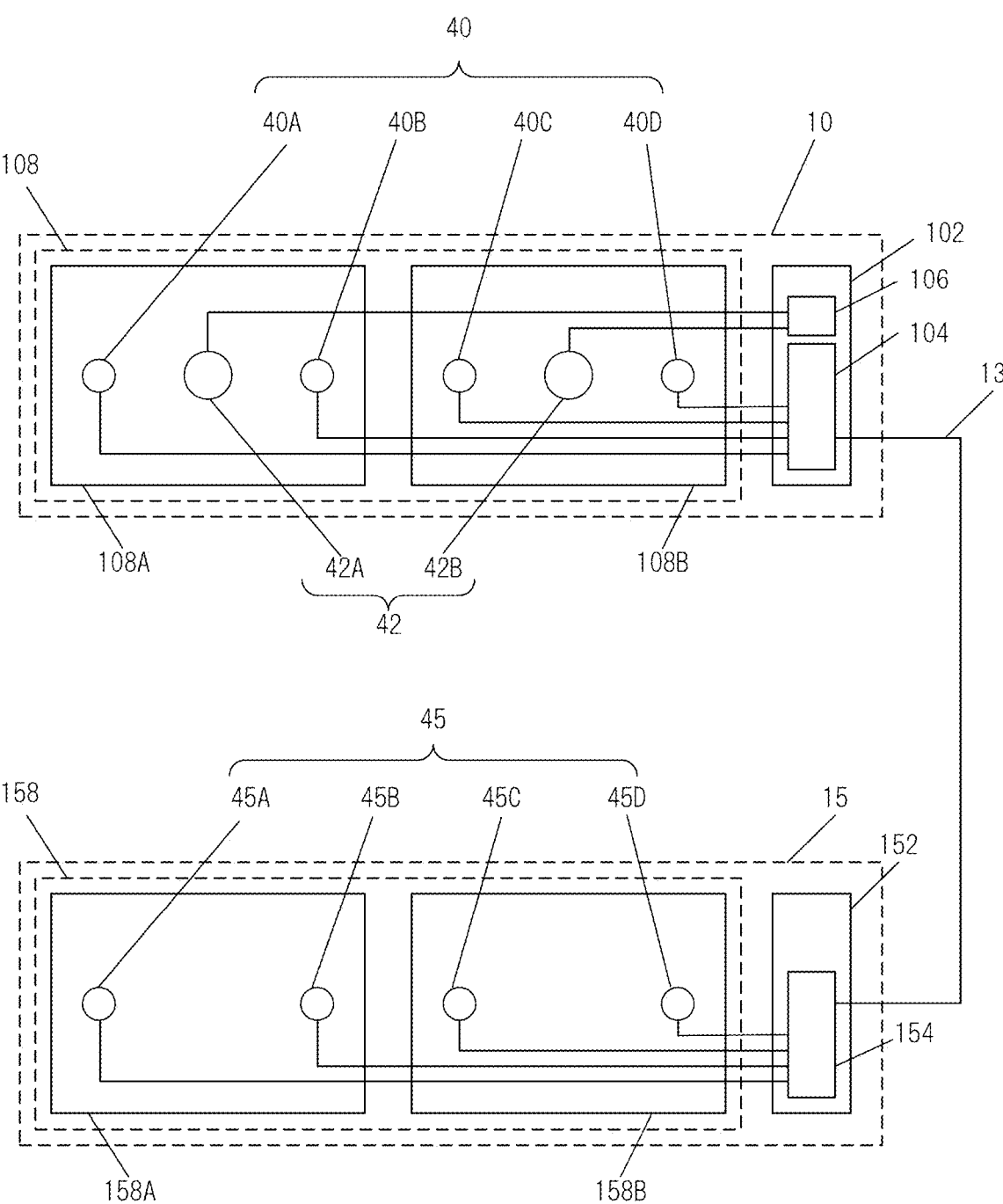
FIG. 3 is a view schematically illustrating configurations of the state acquisition device and the movement acquisition device in the embodiment.

FIG. 3 is a view schematically illustrating the acquisition apparatus 5. For example, the state acquisition device 10 has a control unit 102 and a sensor unit 108. The sensor unit 108 is divided into two housings (members) of a sensor unit 108A and a sensor unit 108B, for example, and a member that can be curved connects the two sensor units 108A and 108B. Since the sensor unit 108 is divided into the two units, the state acquisition device 10 as a whole can be curved near a center thereof.

In addition, for example, by using a foldable flexible member for the sensor unit 108, the acquisition apparatus 5 as a whole can be curved, for example, even when the sensor unit 108 is formed from a single member.

The sensor unit 108 has a first sensor 40 and a second sensor 42. Here, the first sensor 40 is a pressure-sensitive sensor, for example. The first sensor 40 can detect a load related to the first sensor 40. The first sensor 40 can acquire the first state of the user.

For example, the state acquisition device 10 can acquire the following as the first state of the user from the load (load value) that is detected by the first sensor 40.

Whether the user is present on the bed system 1 or has departed therefrom (a state of presence or absence of the user)

The sleeping posture or the posture of the user (for example, whether the user is in a sitting position, the edge sitting position, the supine position, the prone position, the lateral position, or the like on the bed system 1)

The position of the user on the bed system 1 (for example, a position of a center of gravity of the user or the sleeping position of the user)

Another movement of the user (for example, rolling over of the user, movement to an edge of the bed system 1, sleeping of the user with the positions of the head and feet being reversed, or the like).

In addition, the state acquisition device 10 can acquire a change in the state of the user from a change in the load detected by the first sensor 40.

The second sensor 42 is a highly sensitive sensor that can detect slight body movement of the user. Here, compared to the first sensor 40, the second sensor 42 is a sensor that can have a high sensitivity for acquiring the vibration. For example, the second sensor 42, that is, by using the second sensor 42, can detect the slight movement such as the body movement caused by the user's heartbeat or respiration. The second sensor 42 can acquire the biological information as the second state of the user.

As an example of the second sensor 42, an air pad may be provided from a sensor processor 106 provided in the control unit 102 to the sensor unit 108 via an air tube. The air pad may be arranged at the position of the second sensor 42, which has been described with reference to FIG. 3. In addition, a highly sensitive (high-resolution) vibration sensor (a high-resolution three-axis acceleration sensor, a sensor combined with a gyroscope sensor, a high-resolution piezoelectric sensor, or the like) may be arranged at the position of the second sensor 42, which has been described with reference to FIG. 3, and may be connected to a controller 104.

The sensor processor 106 may change types of values acquired from the first sensor 40 and the second sensor 42. For example, the first sensor 40 may measure and output an absolute amount of the load at predetermined timing. The second sensor 42 may measure and output a change amount of the load at predetermined timing. For example, when detecting the user, the first sensor 40 outputs a value that is based on the load applied to the first sensor 40. For example, when detecting a 10-kg load, the first sensor 40 keeps outputting a sensor value that corresponds to 10 kg. Meanwhile, the second sensor 42 stops outputting a sensor value after the 10-kg load is detected and the load is then stabilized.

In this way, the state acquisition device 10 can calculate the center of gravity of the user or the position of the user based on the absolute amount of the load that is output by the first sensor 40, for example. Since a load change caused by the movement of the user is significant, a change in the sensor value that is based on the movement of the load is also significant. Thus, the state acquisition device 10 preferably uses the sensor value of the first sensor 40.

Meanwhile, the state acquisition device 10 can calculate the user's vital signs (the heartbeat and the respiration) based on the change amount of the load that is output by the second sensor 42, for example. A change in the movement (body movement) that is based on the user's vital signs is small. Accordingly, since the second sensor 42 is the highly sensitive sensor in comparison with the first sensor 40, and the sensor value of the load that is based on the body movement shows a small change, the state acquisition device 10 preferably uses the sensor value of the second sensor 42.

Just as described, by using the second sensor 42 that can detect the vibration with the higher sensitivity than the first sensor 40, the state acquisition device 10 can further acquire the biological information of the user from the slight body movement of the user, such as the user's body movement caused by the respiration or the user's body movement caused by the heartbeat.

Here, the first sensors 40 are preferably provided at equally-spaced intervals. The state acquisition device 10 in this embodiment has, as the first sensor 40, four first sensors 40A, 40B, 40C, 40D at equally-spaced intervals. In addition, the state acquisition device 10 in this embodiment has, as the second sensors 42, two second sensors 42A, 42B at equally-spaced intervals. Here, the number of the first sensors 40 and the number of the second sensors 42 merely constitute one example, and the larger number of the first sensors 40 and the second sensors 42 may be provided.

The first sensors 40 are preferably arranged at the equally-spaced intervals on one straight line along a longitudinal direction of the state acquisition device 10. When the state acquisition device 10 is installed on the bed apparatus 3, the first sensors 40 are arranged at the equally-spaced intervals on one straight line along a short direction of the bed apparatus 3. In other words, the first sensors 40 and the second sensors 42 are arranged in a direction that is along a right-left direction of the user.

The number of the first sensors 40 (40A to 40D) provided to the state acquisition device 10 may be the same as the number of third sensors 45 (45A to 45D) provided to the movement acquisition device 15, which will be described below. In addition, the first sensors 40, which are arranged in the state acquisition device 10, and the third sensors 45, which are arranged in the movement acquisition device 15, may be arranged on one straight line along a longitudinal direction of the bed apparatus 3. In other words, the first sensors 40 and the third sensors 45 are arranged along an up-down direction of the user.

The state acquisition device 10 and the movement acquisition device 15 may not be arranged such that the first sensors 40 are strictly arranged on the straight line. For example, in the case where the first sensors 40 and the third sensors 45 are not aligned on the straight line and are misaligned by several centimeters due to attachment positions of the state acquisition device 10 and the movement acquisition device 15, such misalignment is considered to fall within a margin of error, and thus the first sensors 40 and the third sensors 45 are considered to be arranged on the straight line.

The controller 104 receives signals from the first sensor 40 and the second sensor 42. Then, based on the acquired signals (for example, the load value, a vibration level, and the like), the controller 104 can acquire the state of the user (the first state) and the biological information of the user (for example, the heartbeat, the respiration, and the like) (the second state).

The optional movement acquisition device 15 may be connected to the state acquisition device 10 via the cable 13. Similar to the state acquisition device 10, the movement acquisition device 15 has a control unit 152 and a sensor unit 158.

The state acquisition device 10 and the movement acquisition device 15 may be connected wirelessly. As a wireless connection method, any of communication methods such as a wireless LAN, Bluetooth® as near field communication, and Wireless USB may be used.

Similar to the state acquisition device 10, in the movement acquisition device 15, the sensor unit 158 may include two units of a sensor unit 158A and a sensor unit 158B. In addition, the sensor unit 158 has, as the third sensors 45, third sensors 45A, 45B, 45C, 45D. The third sensor 45 is a sensor that can detect the load, and is the same sensor as the first sensor 40 or is the same as the first sensor 40 in performance. A controller 154 of the movement acquisition device 15 calculates the load value based on a signal acquired from the third sensor 45, and sends the load value to the controller 104 of the state acquisition device 10.

Accordingly, when being connected with the movement acquisition device 15, the state acquisition device 10 can acquire the load values from the eight load sensors that are the first sensors 40 and the third sensors 45 provided to the movement acquisition device 15.

In addition, since the movement acquisition device 15 is the optional acquisition device, the movement acquisition device 15 only needs to include bare minimum components in comparison with the state acquisition device 10. For example, the movement acquisition device 15 may not have a highly sensitive sensor corresponding to the second sensor 42 and capable of acquiring the biological information of the user. Furthermore, the controller 154 of the movement acquisition device 15 only needs to have a configuration that is enough to send the load value acquired from the third sensor 45 to the state acquisition device 10.

Sensor Unit

Figure 4:
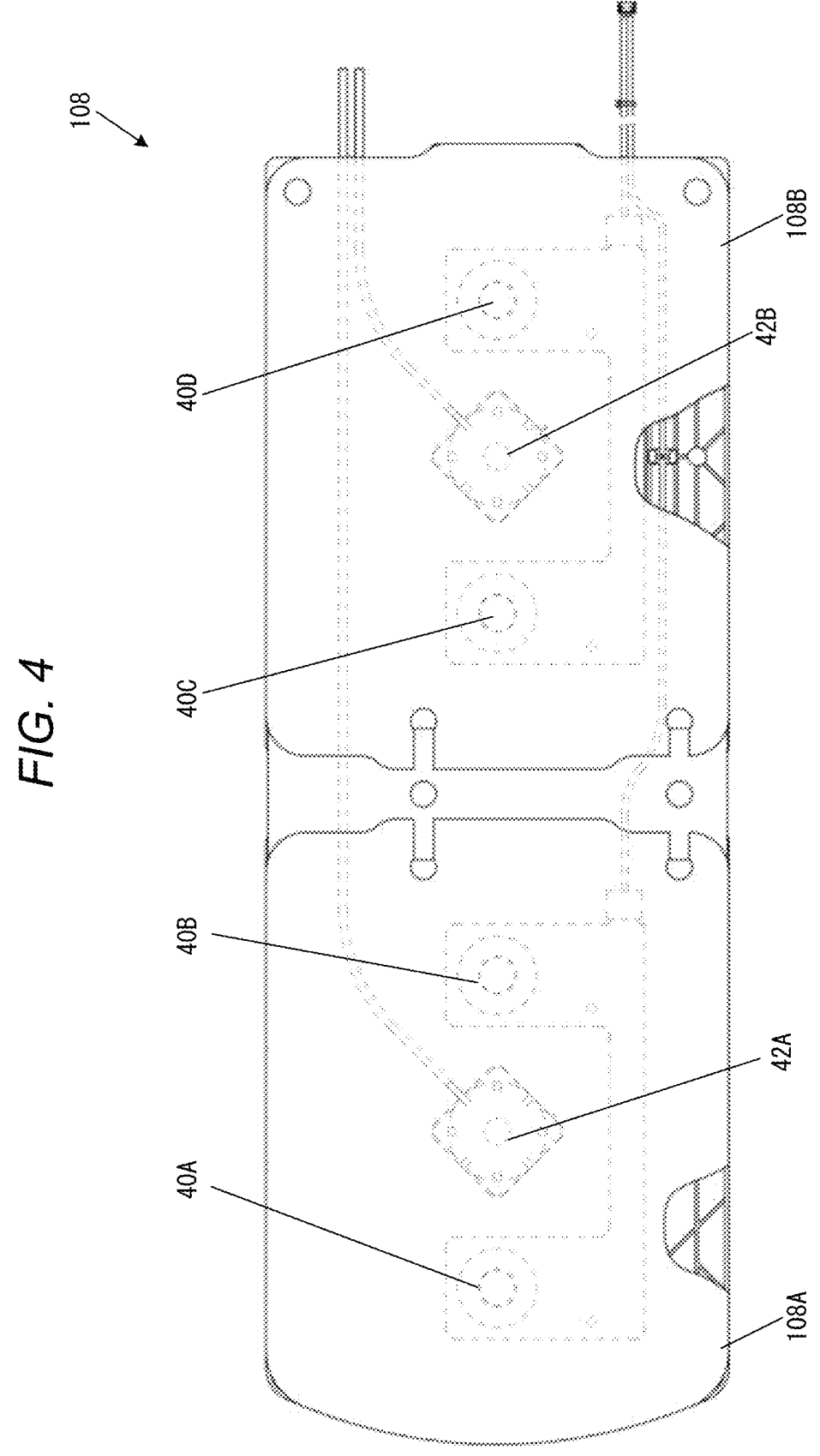
FIG. 4 is a view illustrating a sensor unit in the embodiment.

FIG. 4 and FIGS. 5A to 5E illustrate a configuration of the sensor unit 108. FIG. 4 is a view illustrating the sensor unit 108 of the state acquisition device 10 in the acquisition apparatus 5, for example. FIGS. 5A to 5E illustrate the sensor unit 108B of the sensor unit 108. FIGS. 5A to 5E illustrate arrangement of the first sensors 40 (the first sensors 40C, 40D arranged in the sensor unit 108B in FIGS. 5A to 5E) and the second sensor 42 (the second sensor 42B arranged in the sensor unit 108B in FIGS. 5A to 5E) in a housing 110 of the sensor unit 108B. The housing 110 is a lower housing of the sensor unit 108.

A description will be made on characteristics of the sensor unit 108. The second sensor 42 is arranged substantially at a center of the sensor unit 108. For example, the second sensor 42A is arranged substantially at a center of the sensor unit 108A. The second sensor 42B is arranged substantially at a center of the sensor unit 108B.

In the sensor unit 108, the first sensors 40 are arranged on the straight line along the longitudinal direction of the state acquisition device 10 in a manner to sandwich the second sensor 42. Just as described, the first sensors 40 and the second sensor 42 are preferably arranged on the straight line along the longitudinal direction of the state acquisition device 10. However, the first sensors 40 and the second sensor 42 do not always have to be arranged on the straight line. For example, the second sensor 42 may be arranged at a position that moves upward in FIG. 4.

Figures 5A, 5B, 5C, 5D, 5E, 5F:
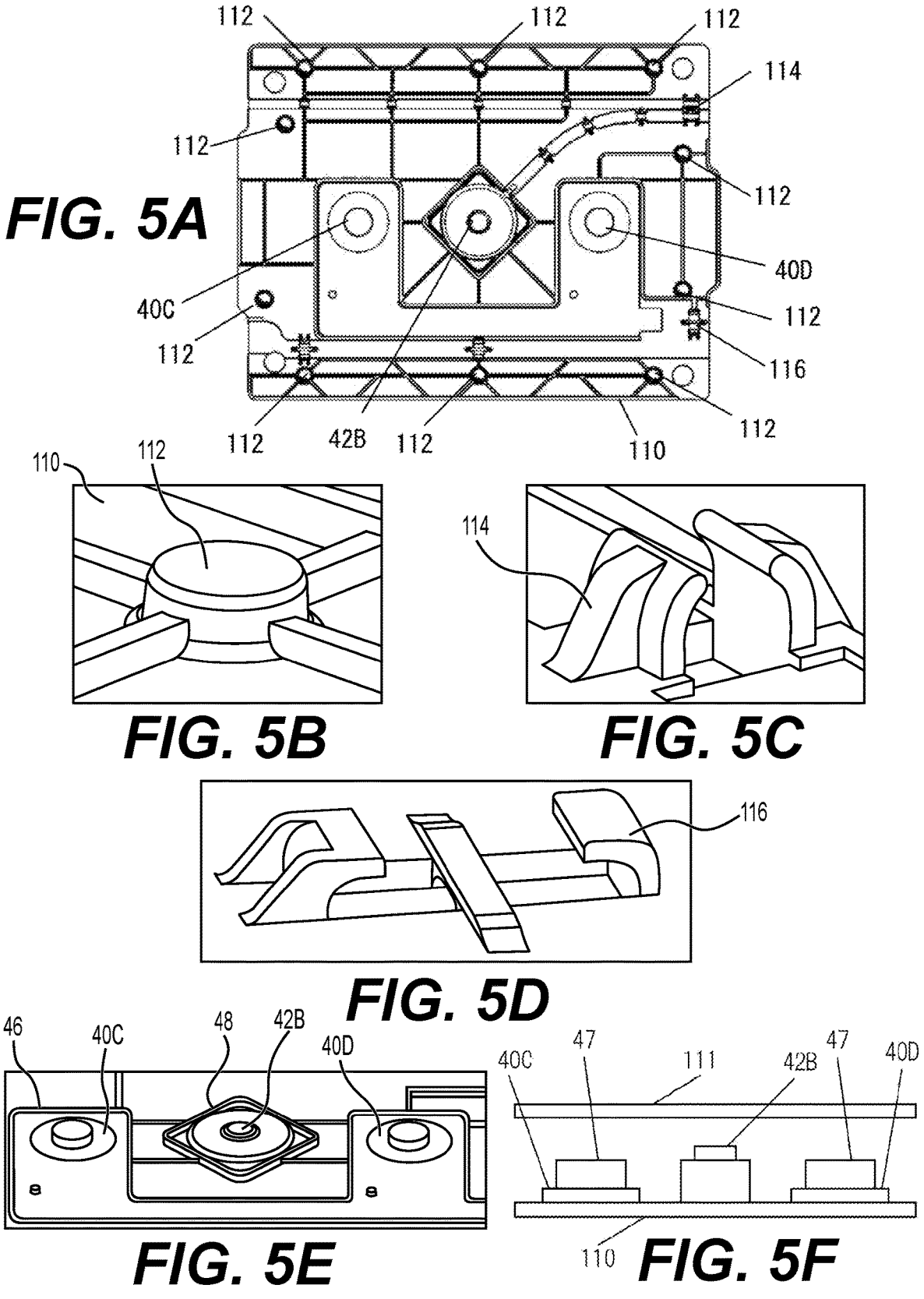
FIGS. 5A to 5F illustrate inside of the sensor unit in the embodiment.

Here, the sensor unit 108 may have a shock absorbing member between an upper housing and the lower housing. For example, as illustrated in FIG. 5A, the housing 110 has shock absorbing sections 112 at plural positions. The shock absorbing section 112 is configured to have the shock absorbing member such as a resin, rubber, urethane, or a sponge, and is preferably provided at a position where the lower housing 110 and the upper housing (not illustrated) are in contact.

FIG. 5B is an enlarged view of an area near the shock absorbing section 112. For example, the shock absorbing section 112 is preferably injection-molded with the housing 110 and is preferably integrally molded by including the shock absorbing member. By integrally molding the shock absorbing section 112 with the housing 110, it is possible to eliminate a manufacturing step of bonding the shock absorbing member to the housing 110.

As the shock absorbing member that is used in the shock absorbing section 112, for example, an anti-slip member such as polyurethane rubber may be used. For example, as the shock absorbing member, the shock absorbing member formed of rubber, polyurethane, or the like, a vibration proof member, or the anti-slip member may be used.

The housing 110 may have a guide section that bundles and guides cables connected to the first sensor 40 and the second sensor 42. For example, as illustrated in FIG. 5A, the housing 110 has a guide section 116 that guides the cable connected to the first sensor 40. The housing 110 also includes a guide section 114 that guides the cable (air tube) connected to the second sensor 42.

The guide section 114 may include a claw member for grasping the cable from both sides to fix the cable. By providing one or more guide sections 114 at positions, through each of which the cable connected to the second sensor 42 runs, the cable (for example, the air tube) can be disposed along the one or more guide sections 114. For example, FIG. 5C is an enlarged view of the guide section 114.

In addition, by providing the guide section 116 at a position, through which the cable connected to the first sensor 40 runs, the cable (for example, the air tube) can be bundled by using the guide section 116. FIG. 5D is an enlarged view of the guide section 116.

The guide section 116 has a wide shape so as to be able to consolidate the two cables connected to the first sensor 40. In addition, the guide section 116 has a partition at a center, and partitioned spaces are each covered with a claw member. In this way, the guide section 116 is configured to be able to hold the two cables at the partitioned spaces. Furthermore, each of the claw members of the guide section 116 is formed to be flat on an upper side. Thus, it is configured to reduce a height of the guide section 116.

FIG. 5E illustrates arrangement of the first sensors 40 and the second sensor 42. FIG. 5E is an enlarged perspective view of a portion corresponding to the first sensors 40C, 40D and the second sensor 42B.

Here, the housing 110 may be formed with a rib 46 at a position corresponding to the first sensor 40. The housing 110 may also be formed with a rib 48 at a position corresponding to the second sensor 42. Provision of the rib 46 and the rib 48 enables easy and precise positioning of the first sensor 40 and the second sensor 42 in the housing 110 at the time of design and manufacturing, for example. In addition, the provision of the rib 46 and the rib 48 can secure strength of the housing 110.

FIG. 5F schematically illustrates cross sections of the first sensors 40 and the second sensor 42. As illustrated in FIG. 5F, the first sensor 40C and the first sensor 40D are provided on the lower housing 110. Here, a pusher 47 may be provided on top of each of the first sensors 40 in consideration of an influence on the second sensor 42 that is installed between the first sensors 40. The pusher 47 is formed from the polyurethane rubber, for example.

When an upper housing 111 contacts the first sensor 40 (for example, the first sensor 40C and the first sensor 40D) and the second sensor 42 (for example, the second sensor 42B), the state acquisition device 10 can detect the load on each of the sensors and can acquire the body movement of the user. Here, in the case where the first sensor 40 is the pressure-sensitive sensor, the pusher 47 is provided between the first sensor 40 and the housing 111 such that the load is applied to a pressure-sensitive portion of the pressure-sensitive sensor. That is, when the load is applied from the upper housing 111, the upper housing 111 pushes the first sensor 40 (the pressure-sensitive sensor) via the pusher 47, and the first sensor 40 can thereby detect the load.

Here, in the case where the pusher 47, which is provided on top of the first sensor 40, is located higher than the second sensor 42, the second sensor 42 cannot detect the body movement of the user correctly, and the state acquisition device 10 cannot acquire the biological information correctly. In addition, when the mattress is placed on the state acquisition device 10, the first sensor 40 possibly makes erroneous detection due to weight of the mattress. Thus, the height of the pusher 47 is preferably lower than the height of the second sensor 42 when being provided on the first sensor 40. The height of the pusher 47 is also preferably higher than a height of the shock absorbing section 112 when being provided on top of the first sensor 40. This is because, when the height of the provided pusher 47 is lower than the height of the shock absorbing section 112, the load is applied to the shock absorbing section 112, which prevents the first sensor 40 from acquiring the load correctly.

Just as described, by appropriately setting the height of the pusher 47 in relation to the second sensor 42, it is possible to prevent the erroneous detection by the first sensor 40 without adversely affecting the acquisition of the biological information of the user. For example, in the case where the height of the pusher 47 is too low, the load cannot be detected. Thus, even when the user is present on the state acquisition device 10, the information on the user cannot be acquired. On the contrary, in the case where the height of the pusher 47 is too high, the first sensor 40 reacts with the mattress, the futon, a blanket, or the like to cause the erroneous detection. Just as described, by appropriately setting the height, the pusher 47 does not move when an object such as a comforter, the blanket, or the like used on the bed apparatus 3 is placed on the state acquisition device 10. The pusher 47 can move when the user having assumed weight is present on the state acquisition device 10.

The sensor unit 158 has substantially the same configuration as the sensor unit 108. Since the second sensor 42 is not provided to the sensor unit 158, a shock absorbing material may be provided at a position corresponding to the position where the second sensor 42 is arranged in the sensor unit 108. In this way, the same housing can be used for each of the sensor unit 108 and the sensor unit 158.

In the housing 110, another cable guide may be provided in an intermediate portion to prevent the movement of the cable. In addition, a cable connection portion in the housing 110 is preferably devised to prevent breakage of a connector or the like therein, which occurs when the cable is twisted or tangled. For example, a rib is preferably raised in the housing 110 to restrict the movement of the cable. Alternatively, the cable may be arranged in the housing 110 such that a bundling strap is used for the cable to restrict the movement of the cable.

Control Unit

FIGS. 6A to 8E illustrate a configuration of the control unit 102. FIGS. 6A to 6E illustrate external appearance and an internal state of the control unit 102, and illustrate a state where a circuit board and the like are assembled, for example. FIGS. 7A to 8E illustrate a case (housing) of the control unit 102. FIGS. 7A to 7C illustrate an upper case of the control unit 102, and FIGS. 8A to 8E illustrate a lower case of the control unit 102.

Figures 6A, 6B, 6C, 6D, 6E:
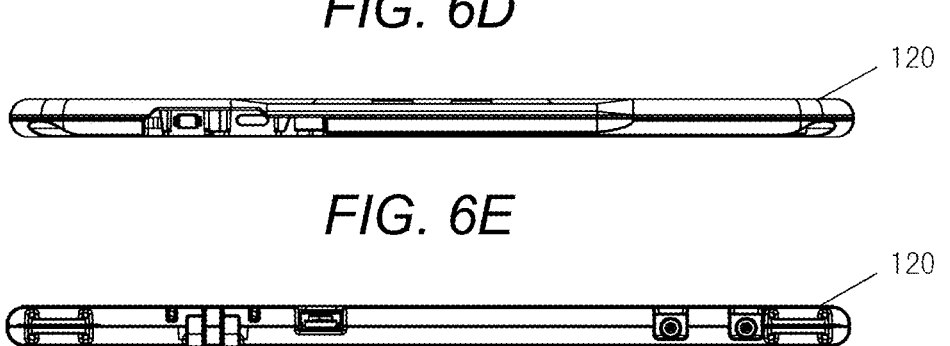
FIGS. 6A to 6E illustrate a controller in the embodiment.

FIG. 6A is a plan view of the control unit 102, and FIG. 6B is a bottom view of the control unit 102. FIG. 6C is an exploded view of the control unit 102. FIG. 6D is a front view of the control unit 102, and FIG. 6E is a back view of the control unit 102.

Figure 7A:
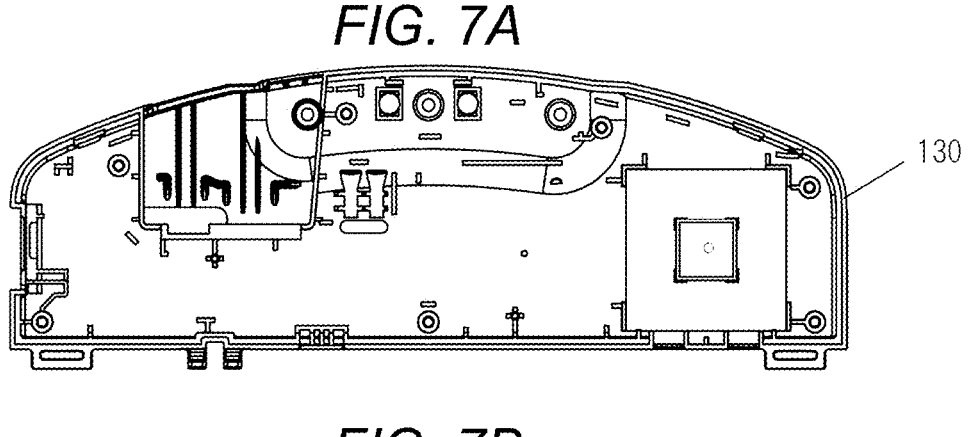
FIGS. 7A to 7C illustrate a housing on an upper case of the controller in the embodiment.
Figure 7B:
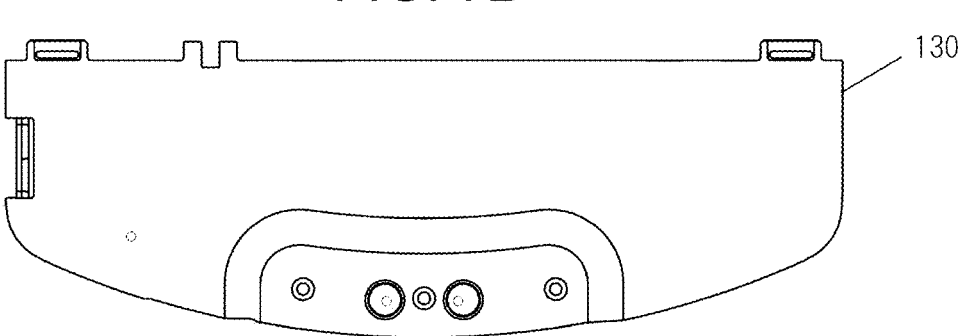
Figure 7C:
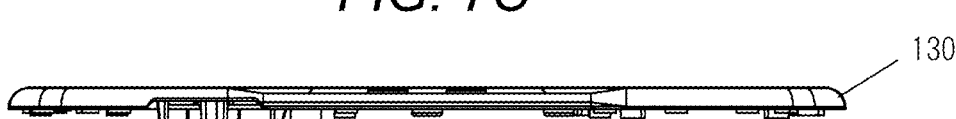

FIGS. 7A to 7C illustrate an upper housing 130 of the control unit 102, and FIGS. 8A to 8E illustrate a lower housing 140 of the control unit 102.

FIG. 7A is a bottom view in which the upper housing 130 is seen from below (a view illustrating an internal side), and FIG. 7B is a plan view in which the upper housing 130 is seen from above (a view illustrating an external side). FIG. 7C is a front view in which the upper housing 130 is seen from the outside (a front view that is seen from an end side of the state acquisition device 10 toward the sensor unit 108).

Figure 8A:
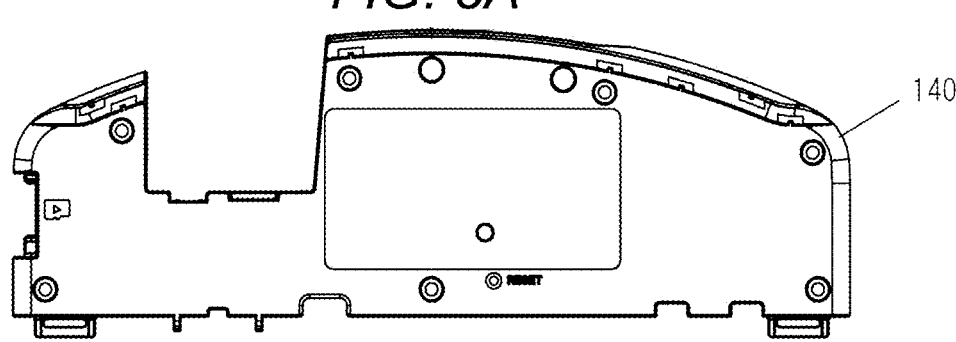
FIGS. 8A to 8E illustrate a housing on a lower case of the controller in the embodiment.
Figure 8B:
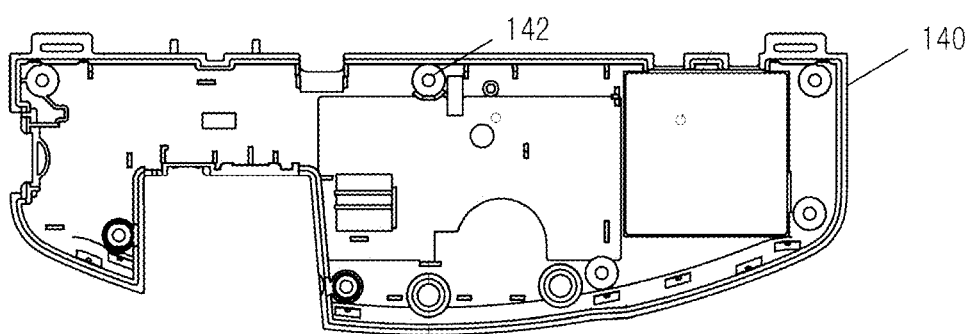
Figure 8C:
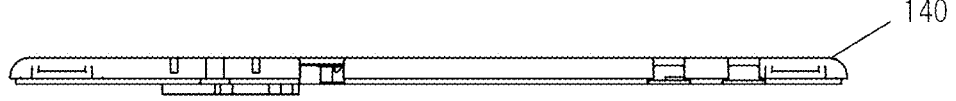
Figure 8D:

FIG. 8A is a bottom view in which the lower housing 140 is seen from below (a view illustrating an external side), and FIG. 8B is a plan view in which the lower housing 140 is seen from below (a view illustrating an internal side). FIG. 8C is a back view in which the lower housing 140 is seen from the inside (a view that is seen from the sensor unit 108 side of the state acquisition device 10). FIG. 8D is a front view in which the lower housing 140 is seen from the outside (a front view that is seen from the end side of the state acquisition device 10 toward the sensor unit 108).

Figure 8E:
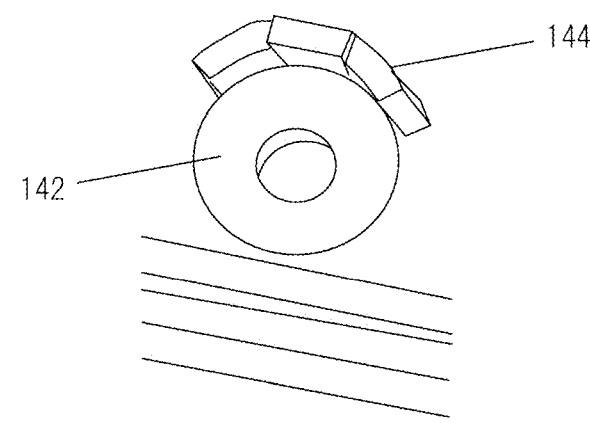

FIG. 8E is an enlarged schematic view of a portion around a coupling hole 142. There is a case where static electricity is generated to the control unit 102 due to rubbing of the mattress or the like against an upper portion of the bed apparatus 3. For this reason, a rib 144 is added around the coupling hole 142 for coupling with a screw or the like. It is possible to prevent generation of the static electricity by providing the rib around the coupling hole 142.

3. Control of Acquisition Apparatus

Next, a description will be made on control of the acquisition apparatus 5.

3.1 Hardware Configuration

Figure 9:
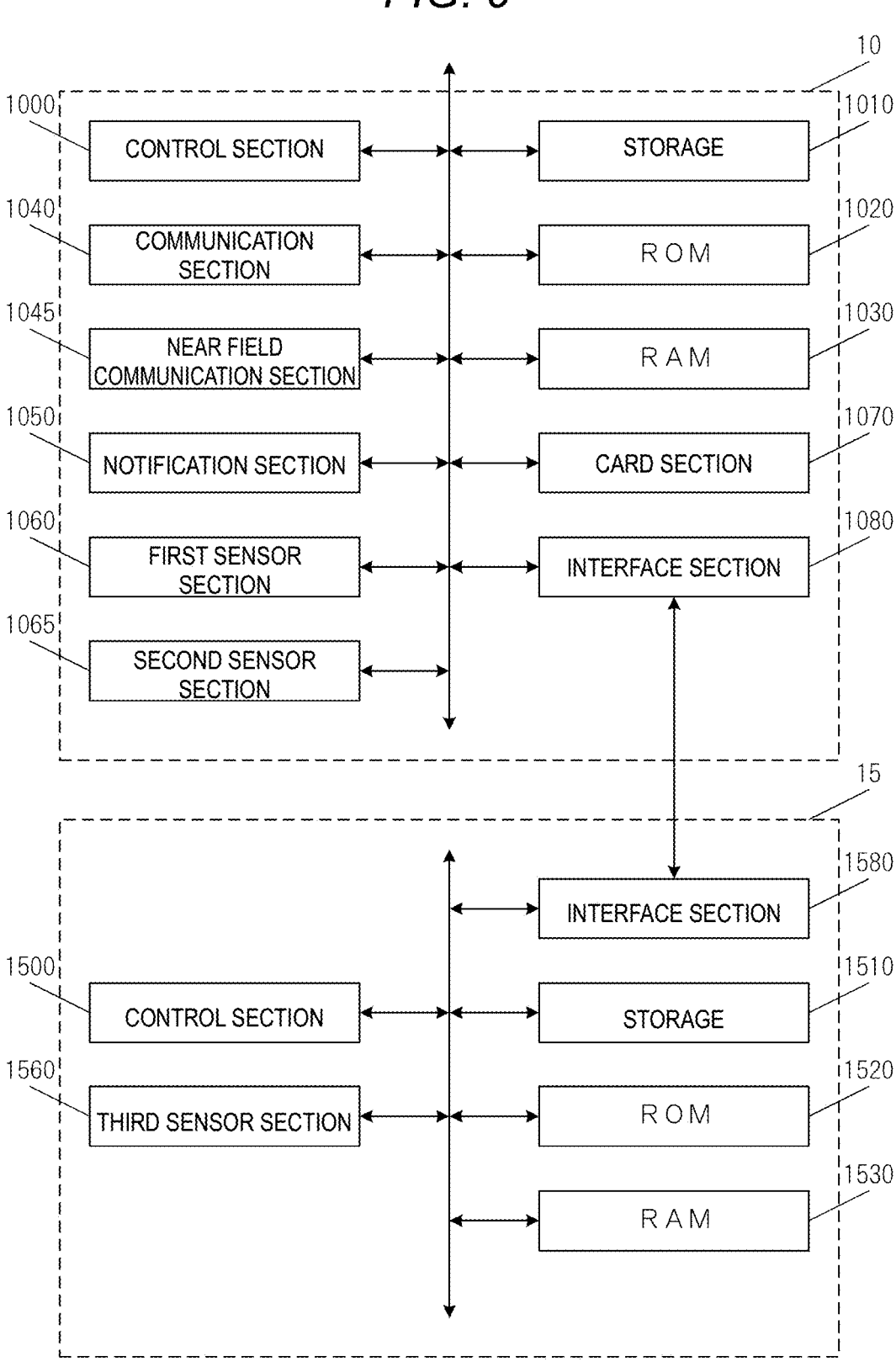
FIG. 9 is a diagram illustrating a functional configuration in the embodiment.

First, a description will be made on control of the state acquisition device 10. FIG. 9 is a view schematically illustrating hardware configurations of the state acquisition device 10 and the movement acquisition device 15.

A description will hereinafter be made on a control section, a storage, ROM, RAM, an interface section, a near field communication section, and a communication section in each of the devices. The state acquisition device 10 and the movement acquisition device 15 may have substantially the same configuration.

A control section 1000 is a functional section for controlling the entire state acquisition device 10. The control section 1000 implements various functions by reading and executing various programs that are stored in the storage and the ROM, and may include one or plural controllers/arithmetic units (central processing units (CPU) or systems on a chip (SoC)). Similar to the control section 1000, a control section 1500 is a functional section for controlling the entire movement acquisition device 15.

A storage 1010 is a nonvolatile storage device that can store the programs and data. For example, the storage 1010 may be a storage device such as nonvolatile memory or may be a storage device such as a solid state drive (SSD). Alternatively, the storage 1010 may be a storage device or a storage medium connectable to the outside or may be a storage device such as a USB flash drive or a memory card, which will be described later. Further alternatively, the storage 1010 may be a storage area on a cloud, for example. The storage 1510 is a nonvolatile storage device in the movement acquisition device 15 and may have substantially the same configuration as the storage 1010 of the state acquisition device 10.

ROM 1020 is nonvolatile memory capable of keeping the program and the data even when power is turned off. The ROM 1020 may store an initial program, BIOS, firmware, and the like. ROM 1520 is nonvolatile memory in the movement acquisition device 15 and may have substantially the same configuration as the ROM 1020 of the state acquisition device 10.

RAM 1030 is main memory that is mainly used when the control section 1000 of each of the state acquisition devices 10 executes processing. The RAM 1030 is rewritable memory that temporarily keeps the programs read from the storage 1010 and the ROM 1020 and the data including results at the time of execution. RAM 1530 is memory in the movement acquisition device 15 and may have substantially the same configuration as the RAM 1030 of the state acquisition device 10.

An interface section 1080 provides an interface that is connected to another sensor device. For example, in this embodiment, the movement acquisition device 15 and the state acquisition device 10 can communicate with each other by connecting the interface section 1080 and an interface section 1580 by a cable. An example of each of the interface section 1080 and the interface section 1580 is an interface using the USB. The state acquisition device 10 and the movement acquisition device 15 may be connected by using the wireless communication (for example, Bluetooth®, Wi-Fi, or the like).

A communication section 1040 is a communication interface that communicates with another device. For example, the communication section 1040 may be a network interface capable of providing wired LAN connection such as Ethernet or wireless connection (for example, the wireless LAN (Wi-Fi or the like)). In this embodiment, the communication section 1040 can communicate with another device via a network NW. The communication section 1040 can also provide a function of being connectable to a mobile network (Long Term Evolution (LTE)/4G/5G/6G).

A near field communication section 1045 makes the wireless communication in a short distance between the state acquisition device 10 and another device. For example, the near field communication section 1045 can make the communication by using Bluetooth® standards.

A notification section 1050 notifies the user, the staff member, and the like. For example, the notification section 1050 may include an optical output section such as the LED, a sound output section such as a buzzer or a speaker, a vibrating element, and the like. For example, the state acquisition device 10 may make a notification by turning on or blinking the LED in the case where the notification section 1050 is the incorporated LED.

In addition to or instead of the above, the notification section 1050 may make the notification by vibration, sound, or the like. For example, the notification section 1050 may make the notification based on the state of the power supply or a communication error of the state acquisition device 10.

When making the notification, the control section 1000 may notify another device (for example, a smartphone used by a family member, the staff member, or the like, a terminal device at a nurses station, or the like) via the communication section 1040. For example, when the notification has to be made to the user, the staff member, or the like, the control section 1000 sends a message or sends a signal outputting an alert to the other device via the communication section 1040 or the near field communication section 1045.

In addition, in the case where the state acquisition device 10 has the notification section 1050, the control section 1000 may execute control such that the notification section 1050 notifies of contents to be notified such contents. For example, the control section 1000 may make the notification by the notification section 1050 that is attached to the state acquisition device 10 (for example, turn on a lamp attached to the state acquisition device 10, emit sound from the buzzer attached thereto, or the like). Alternatively, the notification section 1050 may make the notification from another device (for example, a smart speaker or the like) connected thereto via the near field communication section 1045.

A first sensor section 1060 is the first sensor 40 illustrated in FIG. 3 and the like, and a second sensor section 1065 is the second sensor 42 illustrated in FIG. 3 and the like. A third sensor section 1560 is the third sensor 45 illustrated in FIG. 3 and the like.

A card section 1070 is an interface in/from which a memory card can be inserted/taken out. For example, when a micro SD card is inserted in the card section 1070, the control section 1000 may store necessary information in the micro SD card. In addition, the control section 1000 may store the information in plural locations. For example, when storing the information in the micro SD card, the control section 1000 may also store the information in the storage 1010.

Alternatively, the control section 1000 may also store the information in another device via the communication section 1040 or in the storage area on the cloud.

3.2 Software Configuration

Figure 10:
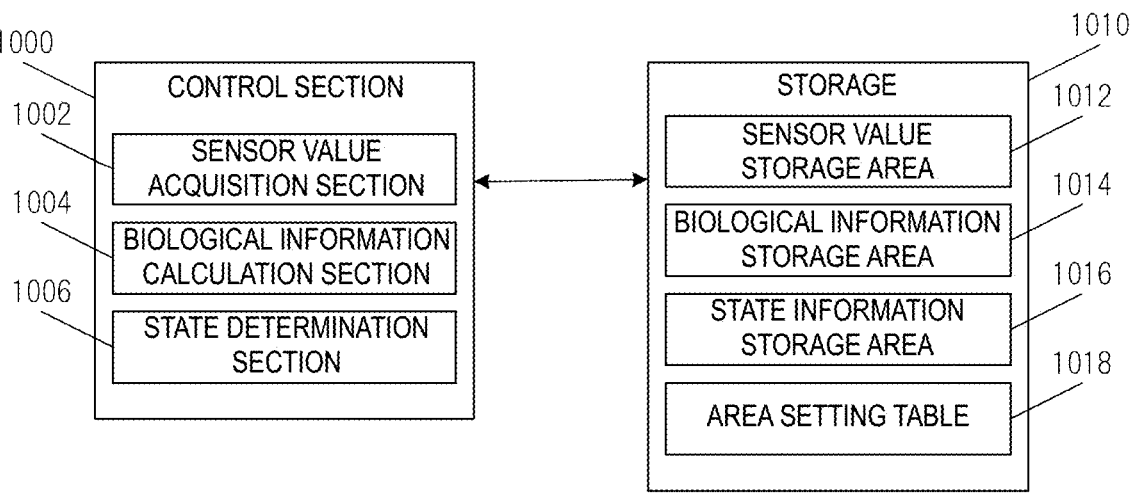
FIG. 10 is a diagram illustrating a software configuration in the embodiment.

FIG. 10 is a diagram illustrating a software configuration of the state acquisition device 10. For example, the control section 1000 of the state acquisition device 10 can implement each of the functions by reading the program from the storage 1010 or the ROM 1020 and executing the program.

A sensor value acquisition section 1002 acquires the sensor values detected by the first sensor 40 and the second sensor 42. The sensor value acquisition section 1002 stores the acquired sensor value in a sensor value storage area 1012. In addition, when the movement acquisition device 15 is connected to the state acquisition device 10, the sensor value acquisition section 1002 acquires the sensor value that is detected by the third sensor 45 of the movement acquisition device 15. Here, the sensor value that is acquired from the first sensor 40 or the third sensor 45 will be referred to as a first sensor value, and the sensor value that is acquired from the second sensor 42 will be referred to as a second sensor value. The first sensor value is the sensor value that is mainly used to determine the position of the user or the posture of the user as the state of the user (to acquire the first state). The second sensor value is the sensor value that is mainly used to acquire the biological information of the user (to acquire the second state).

For example, the sensor value acquisition section 1002 acquires the load values as the first sensor values from the first sensor 40 and the third sensor 45. Here, the sensor value acquisition section 1002 may acquire, as the first sensor value, an absolute value or a variation. In addition, for example, the sensor value acquisition section 1002 may acquire a vibration value (vibration data) or vibration displacement data that is acquired as the second sensor value by the highly sensitive sensor (vibration sensor) from the second sensor 42.

A biological information calculation section 1004 calculates the biological information (a value indicating the biological information) based on the second sensor value that is acquired from the second sensor 42. As the biological information, the heartbeat or the respiration of the user can be calculated, for example. That is, the biological information calculation section 1004 can calculate the second state as the state of the user.

In this embodiment, the control section 1000 (a biological information calculation section 1004) may calculate the biological information by weighting a detection value obtained by a biological information acquisition sensor (for example, the second sensor section 1065 or the second sensor 42) according to the sleeping position or the sleeping posture of the user. For example, the control section 1000 (the biological information calculation section 1004) may double the detection value by the nearest second sensor 42 to the sleeping position, or may halve the detection value by the farthest second sensor 42, so as to calculate the biological information. In addition, the control section 1000 cal-

| culates the biological information by weighting according to the value of the pressure-sensitive sensor.

A state determination section 1006 determines the state of the user. The state of the user can be determined based on the sensor values (the first sensor value and the second sensor value) that are acquired from the first sensor 40, the second sensor 42, and the third sensor 45. The state determination section 1006 can determine the first state as the state of the user.

In addition, the state determination section 1006 may determine a different state by combining the states of the user. For example, in the case where the biological information is not acquired as the state of the user at the time when the state of the user is determined as "sleeping" or "waking-up", the state determination section 1006 may determine that the state of the user is abnormal.

The sensor value storage area 1012 stores the sensor value that is acquired by the sensor value acquisition section 1002. The sensor value may be stored per sensor. In addition, the multiple sensor values are preferably stored in time series. For example, the sensor value is stored in the sensor value storage area 1012 at every predetermined time (every second, every five seconds, or every minute). Furthermore, the sensor value may be stored in association with identification information of the user.

A biological information storage area 1014 stores the biological information of the user. That is, the second state is stored as the state of the user in the biological information storage area 1014. For example, the biological information storage area 1014 stores, as the biological information of the user, biological information values such as the heartbeat rate and the respiratory rate. In addition, the biological information storage area 1014 may also store the biological information that is acquired from another device. For example, the biological information storage area 1014 may also store the biological information such as the body temperature of the user, SpO2 of the user, the blood pressure of the user, and the like.

A state information storage area 1016 stores, among the states of the user, information (the first state of the user) other than the biological information as state information. For example, the state information storage area 1016 may store the state of the bed departure or the bed presence of the user in time series. In addition, the state information storage area 1016 may store the posture of the user as the state of the user and, for example, may store the posture at the edge sitting position. As the posture of the user, in addition to the edge sitting position, the posture at the standing position or the like may be stored. Furthermore, the state information storage area 1016 may store information on sleep as the state of the user. The state information storage area 1016 may store sleeping and waking-up as sleep states of the user in time series. Moreover, the state information storage area 1016 may store the depth of sleep (for example, the REM sleep, the non-REM sleep, and the like) as the sleep state. In addition to the above, the state information storage area 1016 may store, as the state of the user, the position where the user is present (for example, the position on the bed apparatus 3 as will be described below), the posture of the user, and the sleeping posture, for example.

An area setting table 1018 stores areas on the bed apparatus 3 that are virtually set by using the state acquisition device 10.

Herein, a description will be made on the virtual area on the bed apparatus 3 that is set by the area setting table 1018.

Case where State Acquisition Device 10 is Arranged

Figures 11A, 11B, 11C:
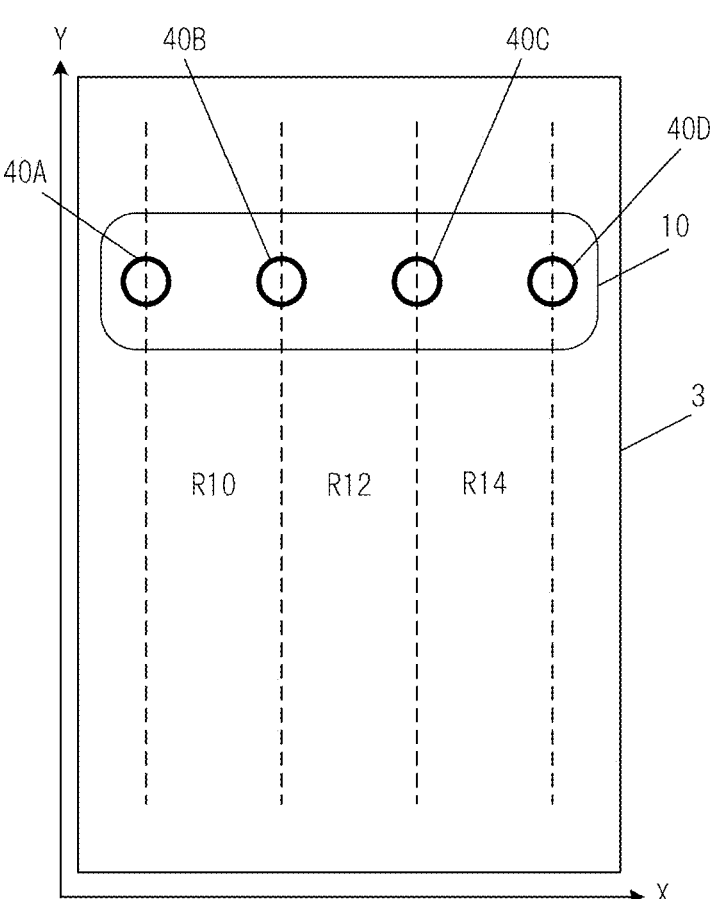
FIG. 11A is a view illustrating an arrangement example of sensors.
FIG. 11B is a table illustrating an example of acquired sensor values.
FIG. 11C is a table illustrating an example of set areas in the embodiment.

FIG. 11A is a view schematically illustrating a relationship between the bed apparatus 3 and the state acquisition device 10. When the state acquisition device 10 is installed on the bed apparatus 3, the state acquisition device 10 acquires the state of the user. For example, the state acquisition device 10 can determine whether the user is present (the bed presence) or absent (the bed departure) on the bed apparatus 3. The state acquisition device 10 can also acquire the state of the user when the user is present on the bed apparatus 3.

Here, the phrase "the user is present on the bed apparatus 3" means a state where the state acquisition device 10 can detect the presence of the user thereon. The phrase "on the bed apparatus 3" refers to a case where the user is present above the sections 20. When the mattress or the like is placed on the sections 20, the phrase "the user on the bed apparatus 3" means the user who is present on the mattress or the like.

The state acquisition device 10 can acquire the states such as the position, the motion, and the posture of the user based on the load value detected by the first sensor 40. FIG. 11B is a table illustrating the sensor values of the first sensors 40 among the sensor values that are stored in the sensor value storage area 1012, for example. In the sensor value storage area 1012, the load values acquired from the first sensors 40 are stored in time series.

Here, the control section 1000 can determine the position of the user with reference to the load values. For example, at "2023/03/10 23:10:00", the load value of the first sensor 40C is the highest as 120, which is followed by the load value of the first sensor 40B as 100. Thus, the control section 1000 finds that the user is located between the first sensor 40B and the first sensor 40C.

At "2023/03/10 23:10:30", the load value of the first sensor 40C and the load value of the first sensor 40D are high as 100. Thus, the control section 1000 finds that the user is located between the first sensor 40C and the first sensor 40D.

Here, as illustrated in FIG. 11A, areas partitioned by the first sensors 40 may be set as the virtual areas. Upon a determination of the virtual area, the control section 1000 determines that the user is in an area R12 at "2023/03/10 23:10:00". Then, at "2023/03/10 23:10:30", the control section 1000 determines that the user is in an area R14.

Figure 12A:
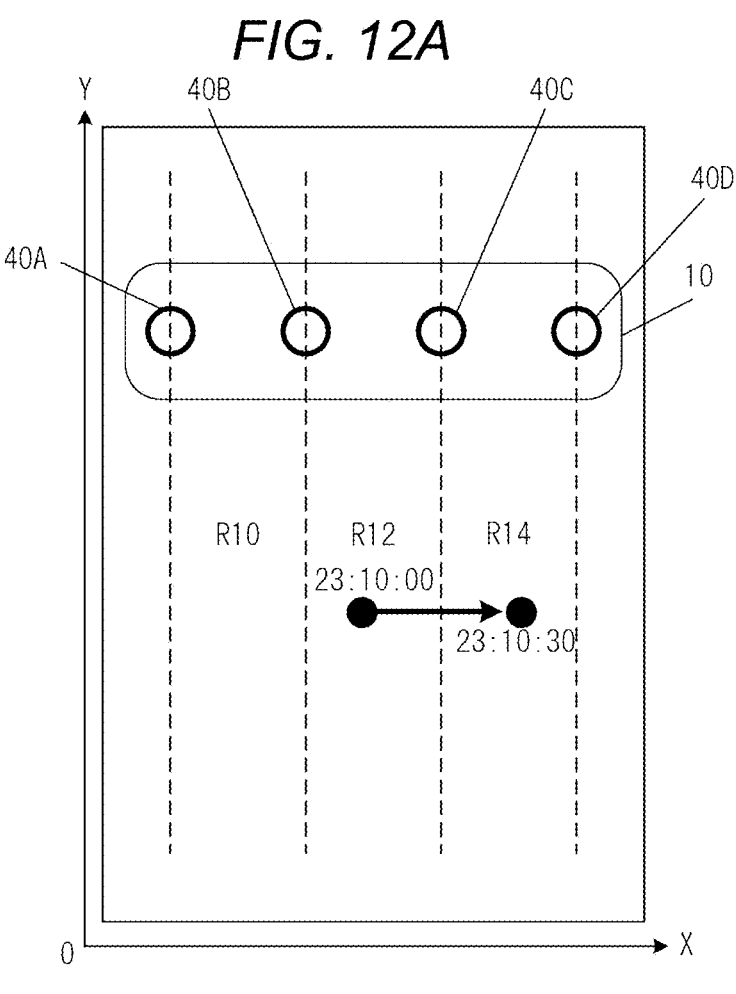
FIG. 12A is a view illustrating motion in the embodiment.
Figure 12B:
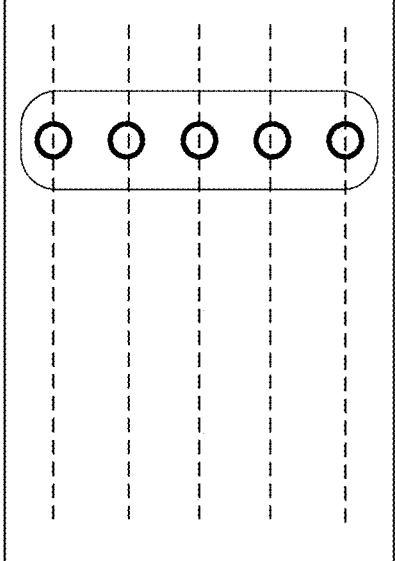
FIG. 12B is a view illustrating another arrangement example of the sensors in the embodiment.
Figure 12C:
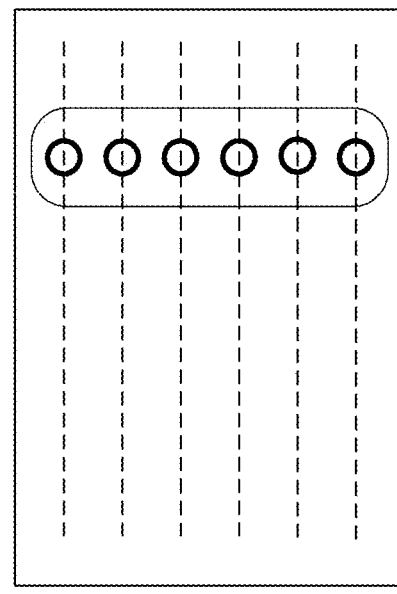
FIG. 12C is a view illustrating further another arrangement example of the sensors in the embodiment.

That is, as illustrated in FIGS. 12A to 12C, the control section 1000 can determine that the user has moved from the area R12 to the area R14.

In addition, the control section 1000 may determine the area by comparing the sensor values of the first sensors 40 with the area setting table 1018. FIG. 11C illustrates an example of the set area setting table 1018. In the area setting table 1018, thresholds of the sensor values are set per area. The control section 1000 determines the area where the user is mainly present by comparing the sensor values output from the first sensor 40 with the area setting table 1018. For example, when comparing the sensor values at "2023/03/10 23:10:00" illustrated in FIG. 11B with the area setting table 1018, the control section 1000 finds that the sensor values of the first sensors 40B 40C exceed the threshold "80". Thus, the control section 1000 determines that the user is mainly present in the area R12.

In addition, the control section 1000 may set a virtual X-Y coordinate space on the bed apparatus 3. Then, the control section 1000 may calculate an X-coordinate and a Y-coordinate of the center of gravity of the user from the load values of the first sensor 40.

For example, when the user is located in an area R10, the X-coordinate of a position of the center of gravity of the user can be calculated by comparing the load values of the first sensor 40A and the first sensor 40B.

Just as described, in this embodiment, the position and the movement of the user can be calculated by arranging the plural (for example, four or more) first sensors 40 on a straight line in a short direction of the sections 20 of the bed apparatus 3. For example, the five first sensors 40 may be arranged as illustrated in FIG. 12B, or the six first sensors 40 may be arranged as illustrated in FIG. 12C.

Figure 13A:
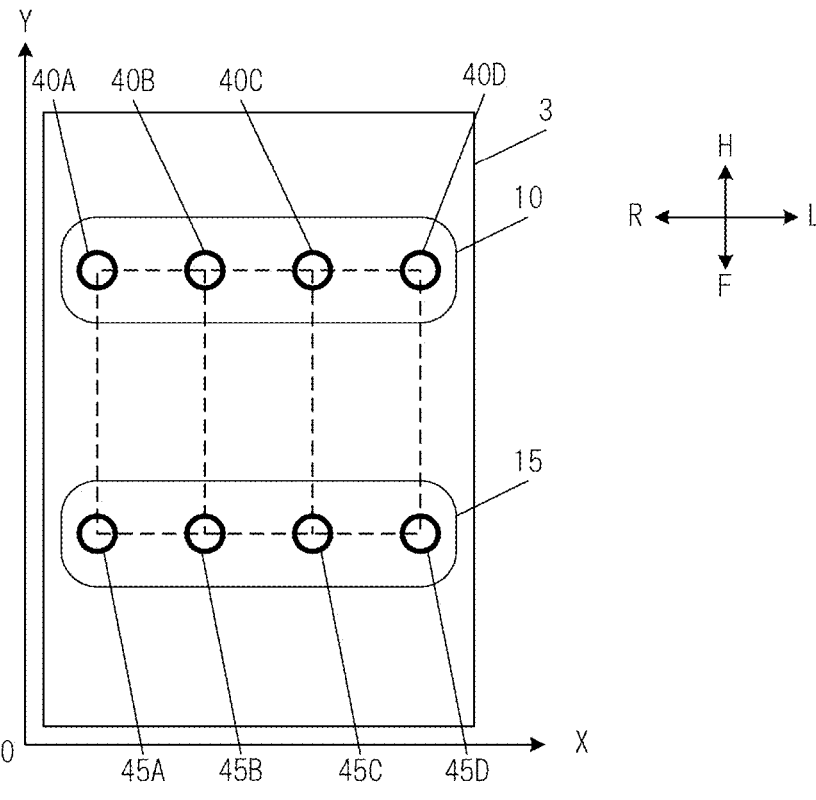
FIG. 13A is a view illustrating further another arrangement example of the sensors in the embodiment.
Figure 13B:
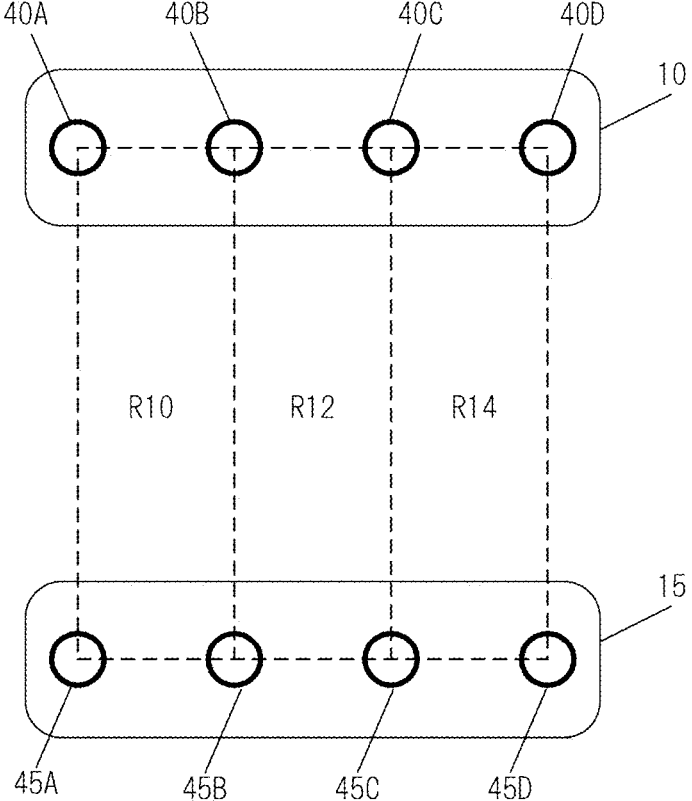
FIG. 13B is a view illustrating motion in the embodiment.

Case where State Acquisition Device 10 and Movement Acquisition Device 15 are Arranged Next, a description will be made on a case where both of the state acquisition device 10 and the movement acquisition device 15 are arranged. FIGS. 13A and 13B schematically illustrate a relationship among the bed apparatus 3, the state acquisition device 10, and the movement acquisition device 15. The state acquisition device 10 and the movement acquisition device 15 acquire the state of the user on the bed apparatus 3.

The control section 1000 can acquire the state of the user based on the sensor values of the first sensors 40 in the state acquisition device 10 and the third sensors 45 in the movement acquisition device 15. Here, the control section 1000 may acquire the state of the user based on the sensor values or the variations of the sensor values. In addition, the control section 1000 may set a virtual area based on the first sensors 40 of the state acquisition device 10 and the third sensors 45 of the movement acquisition device 15 that are placed on the bed apparatus 3.

As a method for setting the virtual area by the control section 1000, for example, a rectangular area with positions of the first sensors 40 in the state acquisition device 10 and the third sensors 45 in the movement acquisition device 15 being vertices may be set. Alternatively, the virtual area may be set at a position where the first sensor 40 and the third sensor 45 are included. Further alternatively, an area where the user on the bed apparatus 3 (the mattress) is present may be set as virtual X-Y coordinates, and each of the areas may be set as the X-Y coordinates. Then, the control section 1000 may calculate the position (the position of the center of gravity) where the load of the user present on the bed apparatus 3 is applied the most from the load values of the first sensors 40 and the third sensors 45, and determine the state of the user based on the position of the center of gravity and the virtually set area.

FIG. 13B is a view only schematically illustrating the state acquisition device 10 and the movement acquisition device 15. Here, the area R10 is an area that includes and is surrounded by the first sensor 40A, the first sensor 40B, the third sensor 45A, and the third sensor 45B. Similarly, the area R12 is an area that includes and is surrounded by the first sensor 40B, the first sensor 40C, the third sensor 45B, and the third sensor 45C. Furthermore, the area R14 is an area that includes and is surrounded by the first sensor 40C, the first sensor 40D, the third sensor 45C, and the third sensor 45D.

The description will be made on an assumption that the virtual area is set for convenience of the description. However, the control section 1000 may not have to actually set the virtual area. For example, in the case where the sensor values (for example, the load value or an index indicating the load value) of the first sensors 40B, 40C and the third sensors 45B, 45C are large at the time of acquiring each of the sensor values, the control section 1000 only needs to determine that a center of the load of the user is present in the area R12. The virtual area in this embodiment is conceptual, and thus the state acquisition device 10 may or may not specifically set the virtual area.

Figures 14A, 14B:
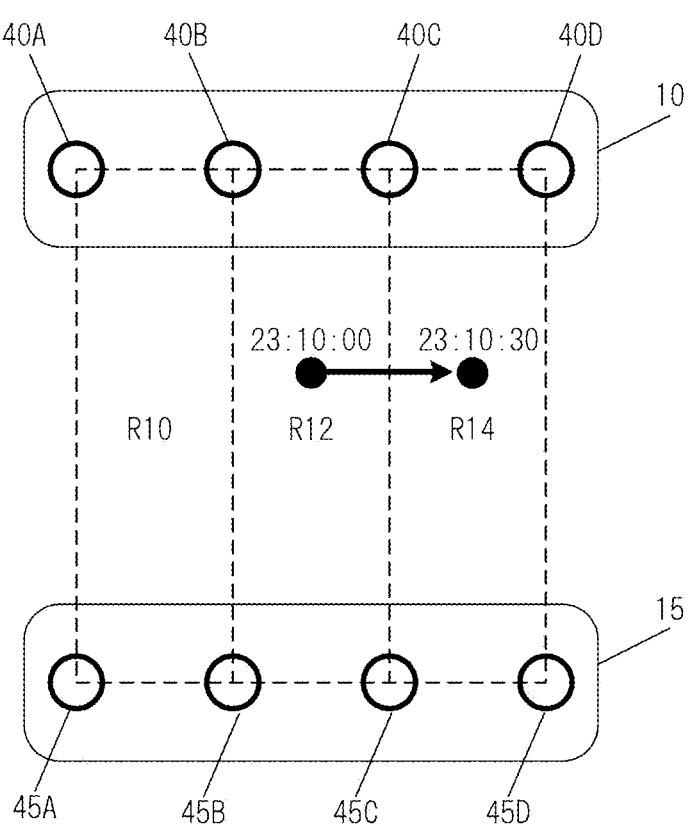
FIG. 14A is a table illustrating another example of the acquired sensor values in the embodiment.
FIG. 14B is a view illustrating the motion in the embodiment.

FIG. 14A is a table illustrating an example of the sensor values of the first sensors 40 and the third sensors 45 that are stored in the sensor value storage area 1012.

For example, with reference to the sensor values at "2023/03/10 23:10:00", since the values of the first sensor 40B, the first sensor 40C, the third sensor 45B, and the third sensor 45C are large, the control section 1000 determines that the user is mainly located in the area R12 on the bed apparatus 3.

Here, with reference to the sensor values at "2023/03/10 23:10:30", since the values of the first sensor 40C, the first sensor 40D, the third sensor 45C, and the third sensor 45D are large, the control section 1000 determines that the user is mainly located in the area R14 on the bed apparatus 3.

In this case, the control section 1000 can determine that the user has moved from the area R12 to the area R14 (has rolled over, has changed the sleeping position, or the like).

In addition, since the sensor values are acquired from the state acquisition device 10 and the movement acquisition device 15, the control section 1000 can more appropriately acquire the state of the user in comparison with a case where only the state acquisition device 10 is arranged. As will be described in detail, for example, it is possible to determine rising of the user and determine the sleeping posture of the user based on changes in the sensor values of the first sensors 40 and the third sensors 45, for example.

3.3 Processing Flow

Next, a description will be made on plural types of processing using the state acquisition device 10 and the movement acquisition device 15.

3.3.1 Notification Processing

Figure 15:
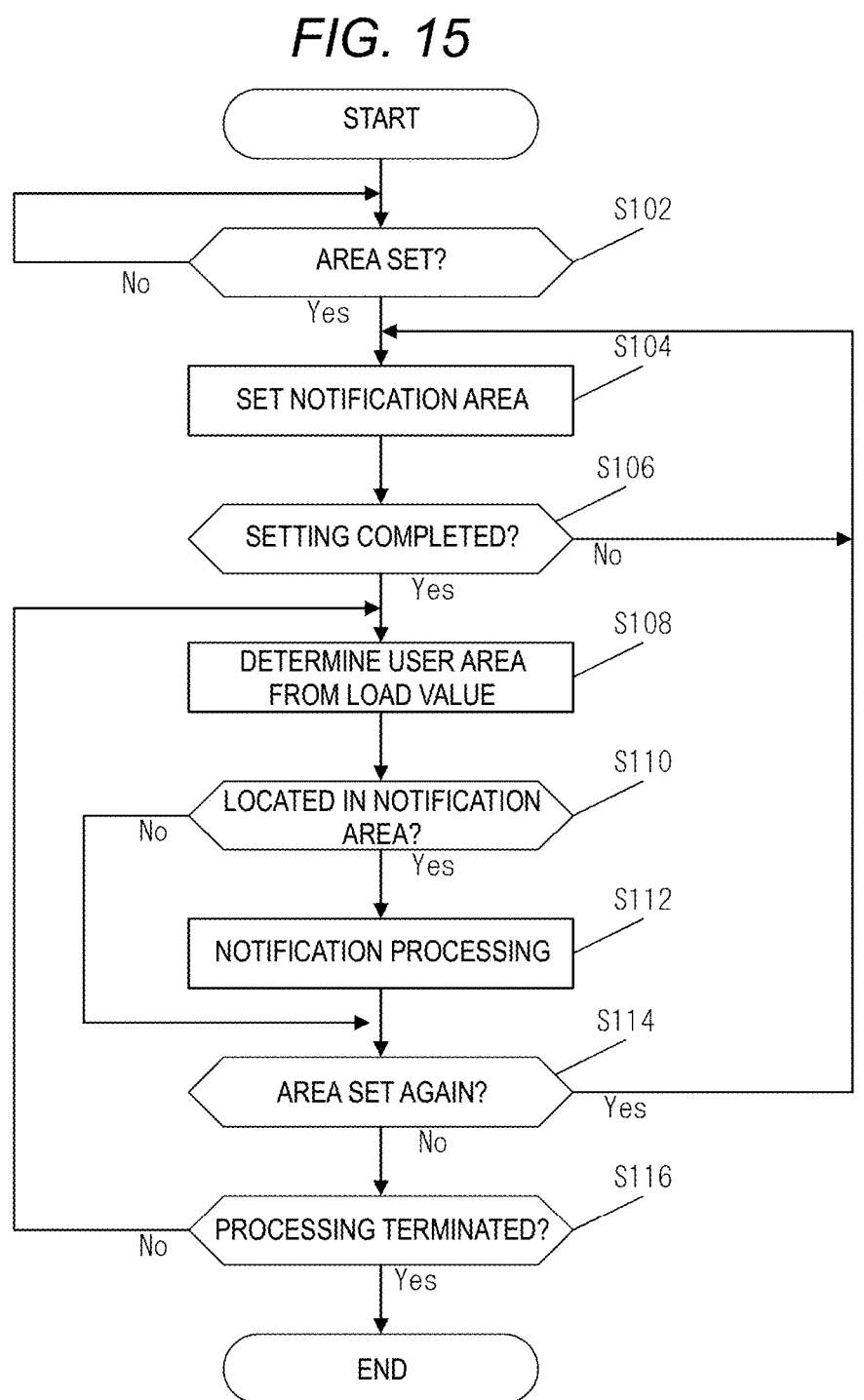
FIG. 15 is a flowchart illustrating processing in the embodiment.

Notification processing will be described with reference to FIG. 15. FIG. 15 is processing executed by the control section 1000.

First, when the areas are set (step S102; Yes), the staff member or the like may set a notification area (in step S104). In other words, the control section 1000 can determine whether each of the areas is the notification area.

Here, various methods for setting the area and setting the notification area by the control section 1000 are considered. Hereinafter, several examples will be described.

(1) Setting by Magnitude of Sensor Value

For example, the control section 1000 can set the notification area by setting the threshold for the sensor value. For example, when the state acquisition device 10 is arranged, the control section 1000 sets the threshold for the first sensor 40A. At this time, when the sensor value of the first sensor 40A exceeds the threshold, it may be notified that there is a risk of falling. In addition, the control section 1000 may set the thresholds of the plural sensor values. For example, in the case where the sensor value of the first sensor 40A is equal to or larger than a first threshold, and the sensor value of each of the first sensors 40 other than the first sensor 40A is equal to or smaller than a second threshold, it may be notified that there is the risk of falling. For example, the threshold for the first sensor 40A is set to "100", and the threshold for each of the first sensors 40 other than the first sensor 40A is set to "30". In the case where the sensor value of the first sensor 40A is larger than the first threshold 100, and the sensor value of each of the other first sensors 40 is smaller than the second threshold 30, the control section 1000 may notify that the user has moved near an edge of the bed apparatus 3.

(2) Setting Based on Area

The control section 1000 sets the areas in the area setting table 1018. At this time, the control section 1000 may set the area including the first sensor 40 as the area. In the case where the area to notify is set among the areas set in the area setting table 1018, the control section 1000 can notify that the user is present in the area to notify.

Figures 16A, 16B, 16C, 16D:
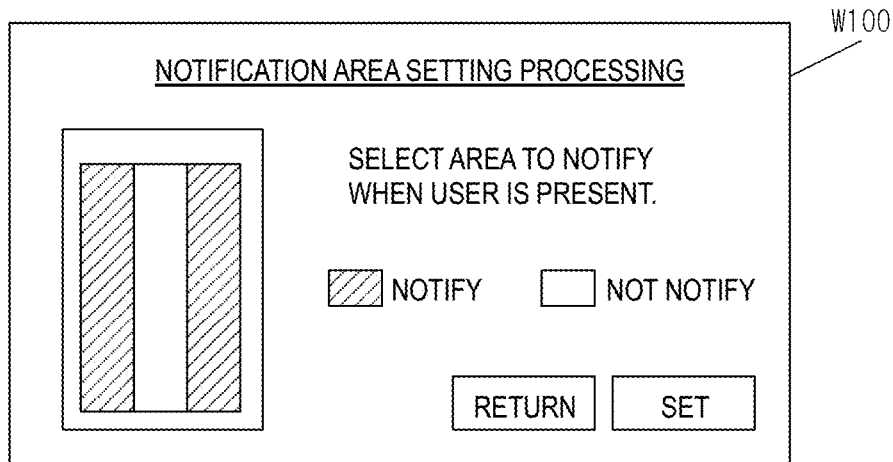
FIG. 16A is a view illustrating an example of a display screen in the embodiment.
FIG. 16B is a table illustrating the motion in the embodiment.
FIG. 16C is a table illustrating the motion in the embodiment.
FIG. 16D is a table illustrating an example of a setting of notification areas in the embodiment.

The notification area can be set by another terminal device, for example. For example, FIG. 16A illustrates an example of a display screen W100 on which the notification area is set. For example, the staff member or the like displays the display screen W100 setting the notification area by running an application of a computer or the smartphone. Then, the user can set whether to make the notification for each of the areas by selecting the area displayed on the display screen W100. The notification area may be set in advance, and thus the staff member or the like may not have to change the settings. The set notification area is stored in the area setting table 1018.

FIG. 16B is a view illustrating an example of the area setting table 1018. In the area setting table 1018, whether to notify is set per area.

In the settings of the notification, not only whether the user is located but also a degree of priority or the like may be set. FIG. 16C is a view illustrating another example of the area setting table 1018. The area setting table 1018 in FIG. 16C differs from that in FIG. 16B in a point that "HIGH" or "LOW" is set with making the notification.

Here, the phrase "NOTIFY (HIGH)" means that the degree of priority of the notification is high. For example, increasing or reducing the degree of priority of the notification can be switched based on any of the following criteria.

(1) Determine by Magnitude of Load Value. For example, in the case where the degree of priority is high, the notification is made when the load value is equal to or larger than the first threshold. In the case where the degree of priority is low, the notification is made when the load value is equal to or larger than the second threshold that is larger than the first threshold. In this way, for the area where the degree of priority (LOW) is set, the notification is not made with the small load value even when the user is located in such an area. For example, in the case where the load value in the area is small, the control section 1000 determines that the risk of falling remains low in comparison with the case where the load value is high.

(2) Determine by Period When Load Value is Changed. For example, in the case where the degree of priority is high, the notification is made when a period in which the user is present in the area exceeds a first period. In the case where the degree of priority is low, the notification is made when the period in which the user is present in the area exceeds a second period that is longer than the first period.

For example, there is a case where the user immediately leaves the notification area after entering the notification area. Thus, for the location with the low risk of falling, period until the notification may be extended.

Next, the control section 1000 determines from the load value which area the user is located (step S108). Here, if the area where the user is located is the notification area, the control section 1000 executes the notification processing (step S110; Yes→step S112).

If the area is set again, the control section 1000 repeatedly executes the processing from step S104 (step S114; Yes→step S104). If the processing is not terminated, the control section 1000 repeatedly executes the processing to determine the area where the user is located from the load value (step S116; No→step S108).

As described above, according to this processing, when the state acquisition device 10 and the movement acquisition device 15 are used, it is possible to set the appropriate area simply by placing the state acquisition device 10 on the bed apparatus 3.

Here, the control section 1000 calculates the center of gravity of the user from the load value and determines the user's area. However, the control section may determine whether the user is located in the notification area by comparing the load value with the center of gravity of the user. FIG. 16D illustrates a table that directly stores thresholds for the sensor values of the first sensors 40. Then, in the case where the sensor value that is acquired from the first sensor 40 matches a condition of the threshold stored in FIG. 16D, the control section 1000 may execute the notification processing.

Figure 17A:
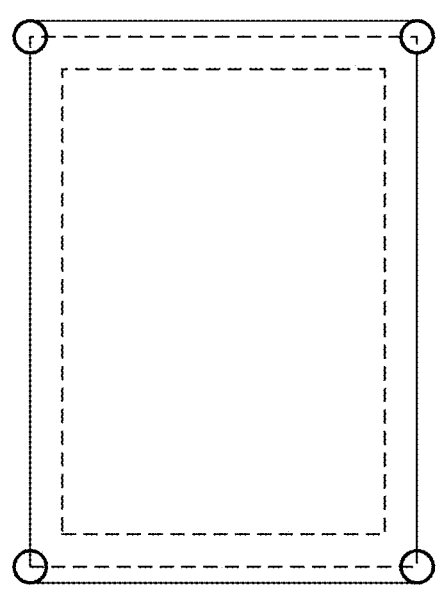
FIG. 17A is a view illustrating a determination method in the related art.

In the contents disclosed in the above-described embodiment, the notification area has conventionally been set for each of the bed apparatuses in order to prevent falling. For example, as illustrated in FIG. 17A, the notification area has to be set for each of the bed apparatuses (an area outside broken lines in FIG. 17A).

However, in the embodiment of the present disclosure, even with the conventional bed apparatus 3, the area can be set, and the appropriate notification can be made without adjusting the position for each of the bed apparatuses 3 simply by installing the state acquisition device 10 on the bed apparatus 3, further connecting the movement acquisition device 15 to the state acquisition device 10, and placing the movement acquisition device 15 on the bed apparatus 3.

In the above-described method, the load value by the sensor is acquired, and the area is determined by using the load value. As another method, the control section 1000 may use the first sensors 40 and the third sensors 45 to acquire the position of the center of gravity of the user and determine the area at the position indicated by the X-Y coordinates.

Figure 17B:
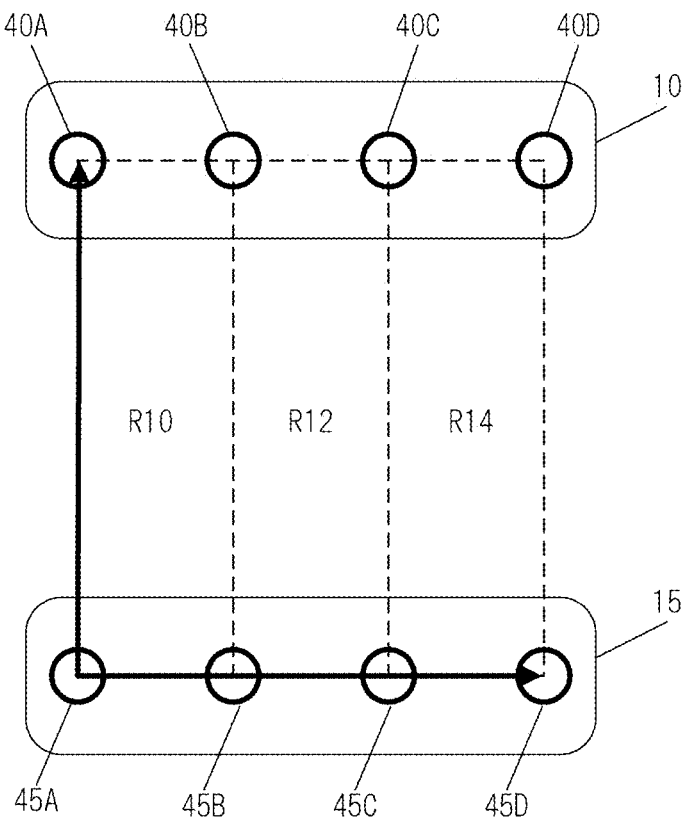
FIG. 17B is a view illustrating a determination method that is based on the area in the embodiment.

For example, as illustrated in FIG. 17B, the X-Y coordinates with the position of the third sensor 45A being (0, 0) are considered. At this time, the area R10 can be identified from position coordinates of the first sensors 40 and the third sensors 45. For example, the area R10 may be set with the coordinates of the first sensor 40A at an upper left corner and the coordinates of the third sensor 45B at a lower right corner.

Just as described, the control section 1000 indicates the position of each of the sensors on the X-Y coordinates. Then, the control section 1000 acquires the coordinates of the position of the center of gravity of the user by using the first sensors 40 and the third sensors 45. The control section 1000 may determine whether to notify the user based on the coordinates of the center of gravity of the user and the coordinates of the area.

In addition, the area may further be divided into plural sub-areas. For example, in FIG. 18A, the area is divided into six sub-areas. Due to a bias in the magnitude of the load value, the control section 1000 sets the areas R10 such that an area closer to the head side (the state acquisition device 10) is an area R10A and an area closer to the foot side (the movement acquisition device 15) is an area R10B. Similarly, the area R12 may be divided into an area R12A and an area R12B, and the area R14 may be divided into an area R14A and an area R14B. By dividing the area into the small areas, the control section 1000 can make the precise notification corresponding to the respective small area.

FIG. 18B illustrates a display screen W110 on which an operation to divide the area is performed. For example, the staff member or the like can perform an operation to freely divide an area B110. The control section 1000 stores, in the area setting table 1018, a load value and coordinates corresponding to each of the sub-areas. In addition, when the staff member or the like selects any of the sub-area, the control section 1000 sets whether such an area is the notification area.

FIG. 18C is a table illustrating further another example of the area setting table 1018. For example, the area setting table 1018 stores the threshold for the sensor value for each of the areas is stored. Then, the control section 1000 only needs to determine the area by comparing each of the sensor values acquired from the first sensors 40 and the third sensors 45 with the respective threshold in the area setting table 1018.

Just as described, according to this embodiment, the staff member or the like can set any area as the notification area. In addition, since the state acquisition device 10 and the movement acquisition device 15 are the devices that are placed on the bed apparatus 3, it is possible to set the areas based on the state acquisition device 10 and the movement acquisition device 15. In this way, the area to be notified in relation to the user can be set regardless of a size or a structure of the bed apparatus 3.

In regard to the above-described division of the area, the state acquisition device 10 and the movement acquisition device 15 are used. However, a single device may be used instead of both thereof. For example, as illustrated in FIG. 11A, the area may be divided only by using the state acquisition device 10.

In the above-described processing, the notification processing has been described as the processing that corresponds to the area. However, another type of processing may be executed. For example, the bed apparatus 3 may be controlled when the user enters the area. For example, the control section 1000 may change a back rising angle of the back section, may change an upper leg angle of the upper leg section, or may change the height of the bed apparatus 3.

The control section 1000 may notify the other device (for example, a nurse call system or a mobile terminal device that is carried by the staff member or the like).

3.3.2 User State Determination

A description will be made on processing to determine the state of the user with reference to FIG. 19. The processing illustrated in FIG. 19 is processing that is acquired by replacing the notification processing that has been described with reference to FIG. 15. The common processing will be denoted by the same reference sign, and a detailed description on such processing will not be made.

The control section 1000 divides the area on the bed apparatus 3 and sets the sub-areas (step S202). As in the above-described processing, the control section 1000 may set the area as a notification target in setting of the area.

Here, the control section 1000 determines, from the load value, the area where the user is present (step S108). When the position of the user is changed, the control section 1000 determines the state of the user (step S206).

The control section 1000 determines that the state of user is changed when the state of the user is determined or when the area as described below is changed.

(1) When the center of the load of the user has been changed beyond the area, the control section 1000 determines that the sleeping position of the user has been changed. For example, the control section 1000 acquires coordinates of the center of the load of the user. Then, when determining that the coordinates of the center of the load have moved out of the area, the control section 1000 determines that the sleeping position of the user has been changed. In addition, when determining that the user has partially or entirely moved out of the area based on changes in the sensor values of the first sensors 40 or changes in the loads detected by the first sensors 40 and the third sensors 45, the control section 1000 determines that the sleeping position has been changed.

FIG. 20A is a view schematically illustrating the first sensors 40 and the sleeping posture of the user. The control section 1000 can determine the sleeping posture of the user based on the changes in the sensor values of the first sensors 40. For example, when the user is at the supine position, the first sensor 40B and the first sensor 40C detect the large load. Thus, the control section 1000 determines that the user is sleeping in the central area (the area R12). Here, when the large load value is detected by the first sensor 40A, the control section 1000 determines that the position of the user has moved to the area R10. That is, the control section 1000 can determine that the user has rolled over to the right (has assumed a right lateral position) from the supine position. At this time, the control section 1000 may determine the sleeping posture of the user by using the value of the second sensor 42. For example, the control section 1000 may determine that the user has been in the lateral position (the right lateral position) when the user is located in the area R10, which is determined from the sensor values of the first sensors 40, and the sensor signal acquired by the second sensor 42 becomes equal to or smaller than the threshold.

The control section 1000 may freely set the threshold for the load value that is detected by the first sensor 40. In this case, for example, the control section 1000 may only determine a particular posture of the user. It may also be set that the control section 1000 does not detect the load in the case where heavy baggage is placed on one lateral side of the bed apparatus 3. For example, as illustrated in FIG. 20B, such a case is assumed in the area setting table 1018 that, despite a fact that the sensor values are output from the first sensor 40A and the first sensor 40B, the high sensor value is output from the first sensor 40D. In this case, such processing may be adopted that the control section 1000 determines that an object or the staff member's hand is placed on an opposite side of the side where the user is present, and thus does not particularly determine the posture of the user (for example, does not make the notification).

The control section 1000 can make the determination further finely by combining the state acquisition device 10 and the movement acquisition device 15. For example, even when the user is sleeping on the foot side of the bed apparatus 3 (the small load is applied to the state acquisition device 10), the control section 1000 can make the appropriate determination.

(2) In the case where the load value has been changed although the area where the center of the load of the user is located remains unchanged, the control section 1000 determines that the user has rolled over. For example, in the case where the control section 1000 detects the changes in the loads, which is detected by the first sensors 40A to 40D and the third sensors 45A to 45D, but the sensor values are not changed (that is, the load of the user is not changed) to such extent that the area where the user is located is changed, the control section 1000 may determine that the user has rolled over.

(3) In the case where the center of the load of the user has moved to the foot side although the area where the center of the load of the user is located remains unchanged, the control section 1000 may determine that the user has sat up. For example, when detecting such changes that the sensor values detected by the third sensors 45A to 45D become larger than those detected by the first sensors 40A to 40D, the control section 1000 may determine that the user has sat up. For example, as illustrated in FIG. 20C, when the user sits up, the sensor values change such that the sensor value becomes large from the head side to the foot side. When acquiring that the sensor values have become large from the head side to the foot side, the control section 1000 may determine that the user has sat up.

(4) When only the third sensor 45 of the movement acquisition device 15 on the user's foot side detects the load, the control section 1000 may determine that the user is in the edge sitting position. For example, in the case where the sensor values that can be detected by the third sensors 45A to 45D are larger than the load values that can be detected by the first sensors 40A to 40D by a threshold or more, the control section 1000 may determine that the user is in the edge sitting position.

(5) When the load of the user has moved out of the area from the edge sitting position, the control section 1000 determines that the user has departed from the bed apparatus 3. For example, in the case where the sensor values detected by the third sensors 45A to 45D are larger than the sensor values detected by the first sensors 40A to 40D by the threshold or more, the control section 1000 determines that the user is in the edge sitting position. At this time, for example, in the case where the sensor value of the third sensor 45A or the third sensor 45D becomes equal to or smaller than the predetermined threshold (that is, the load of the user is no longer detected) after the sensor value changes significantly, the control section 1000 may determine that the load of the user has moved out of the set area on the bed apparatus 3. That is, the control section 1000 may determine that the user has departed the bed apparatus 3.

The control section 1000 stores the state of the user in the state information storage area 1016. For example, the control section 1000 may acquire the state of the user from state information storage area 1016 and output a report or the like.

The control section 1000 may simply determine, as the state of the user, the bed departure, the bed presence, (sleeping or waking-up), the edge sitting position, or sitting up. For example, in the case where the sensor value that is output from the first sensor 40 of the state acquisition device 10 is equal to or larger than the threshold, the control section 1000 may determine the bed presence. On the other hand, in the case where such a sensor value is smaller than the threshold, the control section 1000 may determine undetected. In addition, in the case where the user is present on the bed apparatus 3, the control section 1000 determines sleeping or waking-up as the state of the user.

In the case where the sensor value that is output from the third sensor 45 of the movement acquisition device 15 is equal to or larger than the threshold, the control section 1000 may determine the bed presence. On the other hand, in the case where such a sensor value is smaller than the threshold, the control section 1000 may determine undetected. Alternatively, the control section 1000 may determine the edge sitting position or the bed departure based on the sensor value detected by the movement acquisition device 15. For example, the control section 1500 may determine the edge sitting position or the bed departure based on the load value of the third sensor section 1560. For example, in the case where an increase amount of the load value of the third sensor 45 is increased at a predetermined rate and exceeds the threshold, the control section 1500 may determine that the state of the user is the edge sitting position. Further alternatively, in the case where the load of the user moves to either of the right and left sides of the movement acquisition device 15 and thereafter the load value of the third sensor 45 is rapidly reduced, the control section 1500 may determine that the user has departed the bed apparatus 3.

For example, FIG. 21 illustrates the states of the user that can be determined by the state acquisition device 10 and the movement acquisition device 15. As described above, the state acquisition device 10 can determine, as the state of the user, the bed presence (sleeping or awakening), sitting up, or undetected. Meanwhile, as described above, the movement acquisition device 15 determines, as the state of the user, a disconnected state (disconnection), the bed presence, undetected, the edge sitting position, or the bed departure.

Then, the control section 1000 comprehensively determines the state of the user based on the state of the user that is determined by each of the state acquisition device 10 and the movement acquisition device 15. For example, even in the case where the movement acquisition device 15 does not detect the user, the control section 1000 determines that the state of the user is sleeping when the state acquisition device 10 determines that the state of the user is sleeping. In this way, even in the case where the user rolls over or changes his/her sleeping position by chance and, consequently, the load is not applied to the movement acquisition device 15, the control section 1000 appropriately determines that the state of the user is sleeping.

Meanwhile, even in the case where the state acquisition device 10 determines that the user is present (sleeping or waking up) on the bed apparatus 3, the control section 1000 determines that the user is in the edge sitting position when the movement acquisition device 15 determines that the state of the user is the edge sitting position, or the control section 1000 determines that the user has departed the bed apparatus 3 when the movement acquisition device 15 determines that the state of the user is the bed departure.

As described so far, according to this embodiment, it is possible to determine the state of the user more correctly than the related art by using the state acquisition device 10 on the bed apparatus 3. In addition, it is possible to determine the state of the user further appropriately by using the state acquisition device 10 and the movement acquisition device 15 on the bed apparatus 3 when compared to the case where the state of the user is determined only by the state acquisition device 10.

When using the movement acquisition device 15, the control section 1000 may determine the edge sitting position or the bed departure based on the sensor value acquired from the movement acquisition device 15, in addition to the determination on the state of the user by the state acquisition device 10. Since the control section 1000 can use not only the sensor values of the state acquisition device 10 but also the sensor values of the movement acquisition device 15, it is possible to reduce a period from the bed departure to the notification of the bed departure.

For example, when the applicant executed the processing from the bed departure to the notification of the bed departure only by using the state acquisition device 10, it took about 10 seconds. By connecting the movement acquisition device 15 to the state acquisition device 10, the applicant could reduce the period from the bed departure to the notification of the bed departure to approximately 2 seconds.

4. Other Configurations

In the state acquisition device 10 that has been described in this embodiment, the firmware can be updated via the wireless communication, the wired LAN, or the like. For example, the control section 1000 receives the firmware from a server device or another terminal device via the communication section 1040, and can thereby update the firmware.

The state acquisition device 10 can make various settings and check the information by using the near field communication.

For example, the mobile terminal device is connected to the state acquisition device 10 via the near field communication section 1045 by Bluetooth®. Then, on the terminal device, network information may be set for the state acquisition device 10 by communication through Bluetooth®. In this way, an IP address of the state acquisition device 10 is first set on the mobile terminal device. Then, the mobile terminal device can be connected to the state acquisition device 10 by using an information processor (for example, the computer).

The state acquisition device 10 can use a Bluetooth Low Energy (BLE) beacon. For example, the state acquisition device 10 may periodically acquire environment information such as a temperature and humidity from a device (a thermometer, a hygrometer, a $CO_2$ concentration meter, an illuminometer, or the like) mounted with the BLE beacon. The state acquisition device 10 may periodically send the biological information of the user and the state information of the user to the information processor or the like. The state acquisition device 10 may send such information together with the acquired environment information. The state acquisition device 10 may also send identification information of the worker or the like who has approached the state acquisition device 10.

Various types of the information may be recommended to the staff member or the like by combining the plural state acquisition devices 10. For example, persons with similar sleeping rhythms (an awakening hour and a bedtime hour) may be recommended to be in the same multiple bed room.

The state acquisition device 10 may receive IC tag information of the user by using the BLE and send the IC tag information of the user to the terminal device at the nurses station. In this way, it is possible to detect wandering by the user.

The state acquisition device 10 preferably links the user ID with an ID of the staff member or the like for management. For example, in the case where the user ID received via the BLE or the ID of the staff member or the like differs from the registered ID, the state acquisition device 10 may notify of the wrong room or the wrong place.

In the above-described embodiment, the description has been made on the configuration that the state acquisition device 10 has the four first sensors 40 and the two second sensors 42. For example, as illustrated in a sensor unit 108C of the state acquisition device 10 in FIG. 22, it may be configured to include the two first sensors 40A, 40B as the first sensors 40 and the one second sensor 42A as the second sensor 42.

Figure 22:
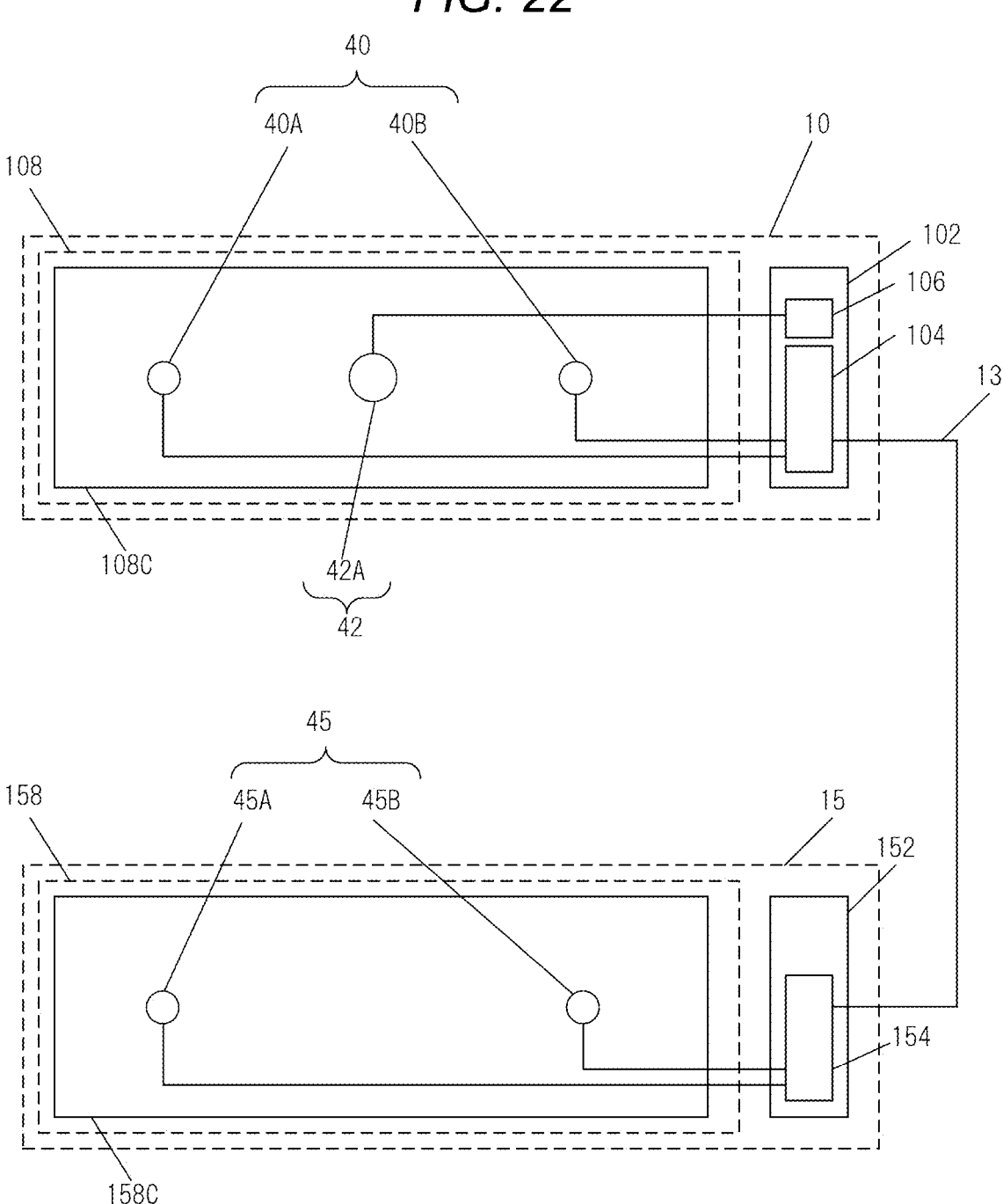
FIG. 22 is a view illustrating different configurations of the state acquisition device and the movement acquisition device in the embodiment.

At this time, as illustrated in FIG. 22, a sensor unit 158C of the optional movement acquisition device 15 may be configured to include the two third sensors 45A, 45B as the third sensors 45.

In the above-described embodiment, the description has been made on that the state acquisition device 10 executes various types of the processing. However, a terminal device 50 that is appropriately connected to the state acquisition device 10 may execute the processing.

Figure 23:
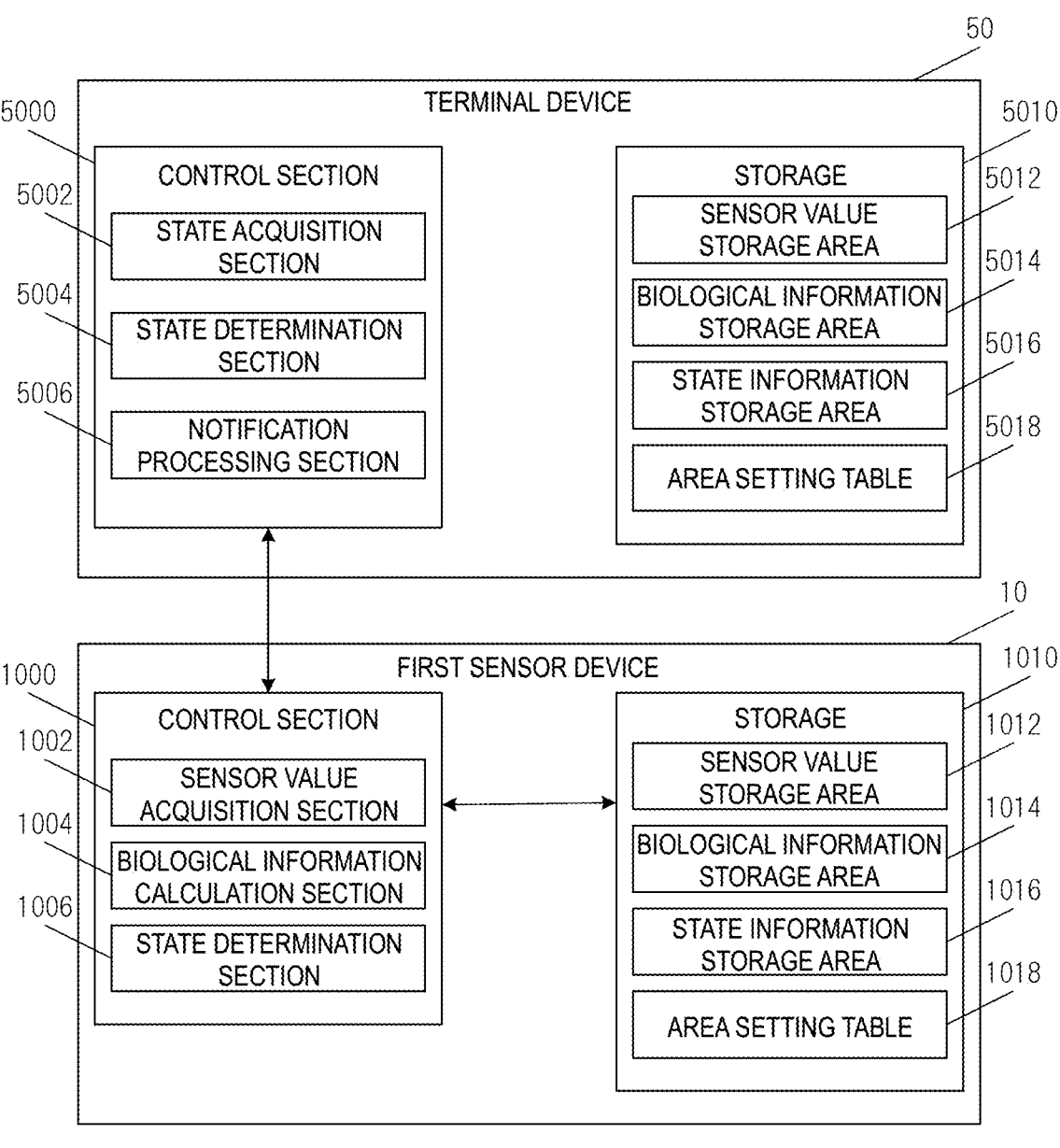
FIG. 23 is a view illustrating a relationship between a terminal device and the state acquisition device in the embodiment.

FIG. 23 is a diagram illustrating a configuration at the time when the terminal device 50 can communicate with the state acquisition device 10. Here, the terminal device 50 may be the information processor such as the computer, a tablet, or the smartphone. The terminal device 50 has the same components provided to the information processor and may include, for example, a control section, a storage, ROM, RAM, a communication section, a near field communication section, a notification section, a display section, and an operation section when necessary.

A control section 5000 of the terminal device 50 can acquire the various types of the information from the state acquisition device 10 via the communication section or the near field communication section. A state acquisition section 5002 can acquire the state of the user, the sensor values, and the biological information from the state acquisition device 10. The terminal device 50 may respectively store the acquired sensor values, the biological information, and the information on the state of the user in a sensor value storage area 5012, a biological information storage area 5014, and a state information storage area 5016.

These types of data stored in a storage 5010 may be stored in either one or both of the storage 5010 and the storage 1010 of the state acquisition device 10. An area set by the terminal device 50 is stored in an area setting table 5018. In this case, the control section 5000 makes a notification by a notification processing section 5006 based on contents set in the area setting table 5018, for example, when the notification is necessary.

In this way, the terminal device 50 may execute the processing that is executed by the state acquisition device 10 (for example, the processing in FIG. 15 and the processing in FIG. 19). In addition, the terminal device 50 can communicate with the one or plural state acquisition devices 10. In this way, for example, even in the case where the plural state acquisition devices 10 are used at the multiple bed room in the hospital or the facility, the terminal device 50 can collectively manage the states of the users.

The terminal device 50 may be connected not only to the state acquisition device 10 but also to the movement acquisition device 15. Alternatively, the terminal device 50 may acquire the information from the movement acquisition device 15 through the state acquisition device 10. The terminal device 50 may acquire the state of the user real time (for example, every second, every five seconds, or the like), or may acquire the state of the user once or plural times at fixed time (for example, the fixed time such as 8 a.m. and/or 9 p.m.) every day. Alternatively, the terminal device 50 may acquire the state of the user from the state acquisition device 10 at any timing.

5. Others

As described above, the following unique effects that are not available in the related art can be expected from the above-described embodiment.

The sheet-type acquisition device has, in addition to the sensor capable of acquiring the body movement of the user, the sensor that senses, in the interlocking manner with the above sensor, the information (for example, the load value) other than the body movement (the vibration) in a non-contact manner. The added sensor can detect the state immediately before the bed departure and can immediately detect the state of the bed departure by adding the sensed information to an algorithm for determining the state of the user by the controller.

In order to exert such an effect, instead of or in addition to an air pressure sensing tube provided to the sheet-type acquisition device, plural sensors (the pressure-sensitive sensors), each of which can detect the person being thereon, are mounted.

Alternatively, in order to exert the above-described effect, instead of or in addition to the air pressure sensing tube, the plural pressure-sensitive sensors (the sensors, a resistance value of each of which varies by a pressure change) are used. By providing plural detection parameters, it is possible to acquire information other than lying down and not lying down (for example, "detection of the sleeping position", "measurement of a frequency of rolling over", "determination on the sleeping posture, "weight measurement", or the like).

In addition to a sensor sheet that is generally provided near the upper back, a sensor sheet that is spread under an area near the lower back is added, and both of the sensor sheets are used together. In this way, slow movement of the user and sleeping of the user on the lower-half side of the mattress can be detected.

Such an effect can also be exerted that, since the state immediately before the bed departure is detected, and the state of the bed departure is detected earlier than before, the staff member or the like using the sensor can notice a user's attempt of the bed departure and can also notice the bed departure by the user earlier than before. In this way, it is possible to prevent wandering of the user in advance and to reduce a risk of the resident being injured by falling.

Since the plural sensors capable of detecting that the person is present thereon are mounted, it is possible to finely detect the state of the user. As a result, the facility staff member can notice and prevent a dangerous event in advance before such an event occurs.

The following may be achieved by providing the system as described above. For example, by using the state acquisition device 10 and the movement acquisition device 15, it is possible to reduce a frequency of occurrence of falling accidents caused by failure of the detection. In addition, in the case where the notification is necessary due to possible falling, the notification can be made further reliably.

Since the sleeping posture can be determined appropriately, it is possible to prevent a pressure ulcer from occurring to the user. For example, the state acquisition device 10 can be configured to forcibly change the posture of the user in information cooperation with an air mattress in the case where the user sleeps in the same posture for a long time.

The state acquisition device 10 may also determine whether bedding is suited for the body by measuring the frequency of rolling over. For example, in the case where the frequency is extremely low, the state acquisition device 10 may suggest (recommend) changing of the mattress to one on which the user can easily roll over.

In addition, the weight may be measured. Then, adjustment of hardness of the air mattress to suit the weight change, the suitable bedding, and the like may be suggested.

6. Modified Examples

The present disclosure is not limited to each of the above-described embodiments, and various modifications can be made thereto.

That is, embodiments that can be implemented by combining technical means appropriately modified within the scope that does not depart from the gist of the present disclosure are also included in the technical scope of the present disclosure.

The above-described embodiments are divided for convenience of the description. However, the embodiments can be combined and implemented within the realm of possibility. The applicants has an intention to acquire the right for any of the techniques disclosed in the present disclosure in the forms of an amendment, a divisional application, and the like.

In the above-described embodiment, the description has been made on, of the acquisition apparatus 5, the state acquisition device 10 as the first acquisition device and the movement acquisition device 15 as the second acquisition device. Here, the first acquisition device acquires the state of the user (the center of the load of the user, the sleeping position, the sleeping posture, the large motion such as rolling over of the user, or the like as the first state, and the vital sign of the user such as the heartbeat or the respiration as the second state) based on the values of the two sensors (the load sensor and the load displacement sensor). Then, the first acquisition device only needs to be able to acquire the state of the user based on the load of the user, which is acquired by the second acquisition device, when necessary. As the second acquisition device, instead of the movement acquisition device 15 described above, the smartphone capable of detecting the load or the load sensor provided to the bed apparatus may be used, for example.

The first acquisition device may be formed by combining plural devices. For example, a device capable of detecting the load (for example, the load sensor provided to the bed apparatus), a wearable terminal device or a smart watch worn by the user whose vital sign (the biological information) can be acquired, and the like may be combined.

The scope of the present disclosure is not limited to the configurations that are explicitly described in the present disclosure, and includes combinations of the techniques disclosed in the present disclosure. In the present disclosure, the configurations, for which the applicant attempts to acquire a patent, are described in the claims.

However, it is not intended that the configuration not described in the claims is excluded from the technical scope.

In the above-described specification, each of the expressions such as "in the case where . . . " and "when . . . " only represents one example, and thus the present disclosure is not limited to the contents described above. Configurations not described with these expressions are also disclosed within the scope that is apparent for those skilled in the art, and the applicant has an intention to acquire the right for such configurations.

Orders of the processing and the data flow described in the present specification are not limited to the described orders. For example, the configuration in which the processing is partially omitted and the configuration in which the order of the processing is changed are also disclosed, and the applicant has an intention to acquire the right therefor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A sheet-type device that can be arranged under a user, the sheet-type device comprising:
   a plurality of first sensors configured to acquire a weight of the user;

a second sensor configured to acquire biological information of the user; and a controller configured to acquire values acquired from the first sensors and to determine a state of the user, wherein the first sensors and the second sensor are arranged in one line along a right-left direction of the user, and the second sensor is arranged between the first sensors, wherein the controller is configured to:
    acquire, from the first sensors, first values corresponding to the absolute amount of load and output continuously when the user is detected; and
    acquire, from the second sensor, second values corresponding to load variation or vibration, the output of which is stopped after the load stabilizes.

2. The sheet-type device according to claim 1, wherein the first sensors and the second sensor are arranged at equally-spaced intervals along the right-left direction.

3. The sheet-type device according to claim 1, wherein the controller is configured
    to calculate a center of the weight of the user from the values acquired from the first sensors, and
    to determine the state of the user from the center of the weight of the user.

4. The sheet-type device according to claim 3, wherein the controller is configured to determine a posture of the user as the state of the user.

5. The sheet-type device according to claim 4, wherein the sheet-type device can be arranged between a bed apparatus and a mattress, and
the controller is configured:
    to determine, as the state of the user, whether the user gets out of or is staying on the bed apparatus, and
    to determine, as the posture of the user, whether the posture of the user is a lying position or an edge sitting position when the user is staying on the bed apparatus.

6. The sheet-type device according to claim 5, wherein the controller is configured:
    to set a plurality of virtual areas on the bed apparatus based on arrangement of the first sensors, and
    to acquire the state of the user based on the center of the weight of the user and the virtual areas.

7. The sheet-type device according to claim 6, wherein the controller is configured to divide the virtual area into a plurality of rectangular sub-areas, each of which includes a corresponding first sensor from the first sensors.

8. The sheet-type device according to claim 7, wherein the controller is configured to set the area, for which a notification is activated if the center of the weight of the user is included therein the set area from the plurality of rectangular sub-areas.

9. The sheet-type device according to claim 7, wherein if the center of the weight of the user moves within the sub-area and the value acquired from the first sensor changes over a threshold or more, the controller is configured to determine that the user has rolled over as the state of the user.

10. The sheet-type device according to claim 1 further comprising:
    a communicator including a third sensor to acquire the weight of the user and can be connected to a sheet-type movement acquisition device arranged under the user, wherein the controller is configured:
    to acquire a value acquired from the third sensor, and
    to determine the state of the user from the value acquired from the first sensor and the value acquired from the third sensor.

11. The sheet-type device according to claim 10, wherein if the value acquired from the first sensor is reduced and the value acquired from the third sensor is increased, the controller is configured to determine that the user has sat up as the state of the user.

12. The sheet-type device according to claim 10, wherein the controller is configured to set a plurality of virtual areas on the bed apparatus based on arrangement of the first sensors and the third sensor, and to set an area for which a notification is activated if the center of the weight of the user is included therein the set area, wherein the plurality of virtual areas are divided along the longitudinal direction of the user's body.

13. The sheet-type device according to claim 1, further comprising a presser disposed above the first sensors, wherein the height of the presser, when disposed above the first sensor, is lower than the height of the second sensor and higher than the height of a cushioning part of the sheet-type device.

14. The sheet-type device according to claim 1, wherein the controller is configured to calculate the biological information by applying a weight to a detection value of the second sensor according to the sleeping position or sleeping posture of the user.

15. A system comprising:
    a first sheet-type device that can be arranged on a bed apparatus and in which a plurality of first pressure-sensitive sensors are arranged in a longitudinal direction; and
    a second sheet-type device that can be arranged on the bed apparatus and in which a plurality of second pressure-sensitive sensors are arranged in a longitudinal direction, wherein
    the first sheet-type device is arranged at a first position of the bed apparatus such that the first pressure-sensitive sensors are arranged at equally-spaced intervals along a width direction of the bed apparatus,
    the second sheet-type device is arranged at a second position of the bed apparatus such that the second pressure-sensitive sensors are arranged at equally-spaced intervals along the width direction of the bed apparatus, the second position being different from the first position and
    the first sheet-type device is configured:
        to acquire, from the second sheet-type device, values acquired by the second pressure-sensitive sensors, and
        to acquire a state of the user on the bed apparatus based on the values acquired from the first pressure-sensitive sensors and values acquired from a second acquisition device, and
        wherein the first sheet-type device further comprises a third sensor configured to acquire biological information of the user, the third sensor being arranged in one line along the width direction of the bed apparatus and being arranged between the first pressure-sensitive sensors, and
        wherein the first sheet-type device's controller is configured to:
            acquire, from the first and second pressure-sensitive sensors, first values corresponding to the absolute amount of load and output continuously when the user is detected; and acquire, from the third sensor, second values corre-
sponding to load variation or vibration, the output
of which is stopped after the load stabilizes, and
acquire the state of the user on the bed apparatus
based on the first values and the second values.

16. The system according to claim 15, wherein the third
sensor is a sensor configured to detect vibration with higher
sensitivity than the first pressure-sensitive sensors.

\* \* \* \* \*